(12) United States Patent
Dabrowiak

(10) Patent No.: US 9,278,023 B2
(45) Date of Patent: Mar. 8, 2016

(54) SYSTEM AND METHOD FOR MANAGEMENT OF BODY TEMPERATURE

(71) Applicant: ZOLL CIRCULATION, INC., Sunnyvale, CA (US)

(72) Inventor: Jeremy Dabrowiak, Sunnyvale, CA (US)

(73) Assignee: Zoll Circulation, Inc., San Jose, CA (US)

( * ) Notice: Subject to any disclaimer, the term of this patent is extended or adjusted under 35 U.S.C. 154(b) by 194 days.

(21) Appl. No.: 13/715,701

(22) Filed: Dec. 14, 2012

(65) Prior Publication Data

US 2014/0172050 A1    Jun. 19, 2014

(51) Int. Cl.
| A61F 7/12 | (2006.01) |
| A61F 7/00 | (2006.01) |
| A61F 7/02 | (2006.01) |

(52) U.S. Cl.
CPC .................. *A61F 7/12* (2013.01); *A61F 7/0085* (2013.01); *A61F 2007/0295* (2013.01); *A61F 2007/126* (2013.01)

(58) Field of Classification Search
CPC  A61F 2007/0054–2007/0058; A61F 2007/12; A61M 2205/36; A61M 2205/3603; A61M 2205/3673
USPC ..................................... 607/105–107; 606/21
See application file for complete search history.

(56) References Cited

U.S. PATENT DOCUMENTS

| | | |
|---|---|---|
| 2,308,484 A | 1/1943 | Auzin et al. |
| 3,088,288 A | 5/1963 | Elfving |
| 3,369,549 A | 2/1968 | Armao |
| 3,425,419 A | 2/1969 | Dato |
| 3,726,283 A | 4/1973 | Dye et al. |
| 3,788,328 A | 1/1974 | Alley et al. |
| 3,918,458 A * | 11/1975 | Nethery ......................... 607/104 |
| 3,995,617 A | 12/1976 | Watkins et al. |
| 4,014,317 A | 3/1977 | Bruno |
| 4,038,519 A | 7/1977 | Foucras |
| 4,111,209 A | 9/1978 | Wolvek et al. |

(Continued)

FOREIGN PATENT DOCUMENTS

| | | |
|---|---|---|
| AU | 730835 B2 | 3/2001 |
| AU | 756115 B2 | 1/2003 |

(Continued)

OTHER PUBLICATIONS

Long, R., "Regional Cranial Hypothermia in the Prevention of Cerebral Ischemic Damage During Carotid Occlusion," Review of Surgery, May-Jun. 1966, pp. 226-228, vol. 23, No. 3.

(Continued)

*Primary Examiner* — Ronald Hupczey, Jr.
*Assistant Examiner* — Yasamin Ekrami
(74) *Attorney, Agent, or Firm* — Rutan & Tucker LLP; John K. Fitzgerald

(57) ABSTRACT

A system and method for adding or removing heat from a heat exchange fluid circulating between an external heat exchanger and an intravascular heat exchange catheter is described. The system includes a two stage cooling system providing for a high rate of cooling in one stage and a lower rate of cooling in a second stage. Both stages may be used to provide maximal cooling while the second stage is used to provide improved control of the cooling rate as a target temperature is approached. The second stage may also be used to provide heat to the heat exchange fluid.

18 Claims, 17 Drawing Sheets

(56) References Cited

U.S. PATENT DOCUMENTS

| | | | |
|---|---|---|---|
| 4,246,932 A | 1/1981 | Raines | |
| 4,298,006 A | 11/1981 | Parks | |
| 4,393,863 A | 7/1983 | Osterholm | |
| 4,445,514 A | 5/1984 | Osterholm | |
| 4,445,887 A | 5/1984 | Osterholm | |
| 4,445,888 A | 5/1984 | Osterholm | |
| 4,446,154 A | 5/1984 | Osterholm | |
| 4,446,155 A | 5/1984 | Osterholm | |
| 4,450,841 A | 5/1984 | Osterholm | |
| 4,451,251 A | 5/1984 | Osterholm | |
| 4,470,407 A | 9/1984 | Hussein | |
| 4,540,402 A | 9/1985 | Aigner | |
| 4,657,532 A | 4/1987 | Osterholm | |
| 4,661,094 A | 4/1987 | Simpson | |
| 4,662,383 A | 5/1987 | Sogawa et al. | |
| 4,672,962 A | 6/1987 | Hershenson | |
| 4,686,085 A | 8/1987 | Osterholm | |
| 4,701,166 A | 10/1987 | Groshong et al. | |
| 4,705,501 A | 11/1987 | Wigness et al. | |
| 4,748,979 A | 6/1988 | Hershenson | |
| 4,754,752 A | 7/1988 | Ginsburg et al. | |
| 4,758,431 A | 7/1988 | Osterholm | |
| 4,769,005 A | 9/1988 | Ginsburg et al. | |
| 4,795,423 A | 1/1989 | Osterholm | |
| 4,804,358 A | 2/1989 | Karcher et al. | |
| 4,819,655 A | 4/1989 | Webler | |
| 4,830,849 A | 5/1989 | Osterholm | |
| 4,857,054 A | 8/1989 | Helfer | |
| 4,873,978 A | 10/1989 | Ginsburg | |
| 4,892,095 A | 1/1990 | Nakhgevany | |
| 4,892,519 A | 1/1990 | Songer et al. | |
| 4,899,741 A | 2/1990 | Bentley et al. | |
| 4,909,252 A | 3/1990 | Goldberger | |
| 4,919,134 A | 4/1990 | Streeter | |
| 4,920,963 A | 5/1990 | Brader | |
| 4,941,475 A | 7/1990 | Williams et al. | |
| 4,960,103 A | 10/1990 | Urso | |
| 4,962,761 A * | 10/1990 | Golden | 607/104 |
| 4,963,130 A | 10/1990 | Osterholm | |
| 4,976,691 A | 12/1990 | Sahota | |
| 4,981,691 A | 1/1991 | Osterholm et al. | |
| 4,995,863 A | 2/1991 | Nichols et al. | |
| 5,011,488 A | 4/1991 | Ginsburg | |
| 5,019,075 A | 5/1991 | Spears et al. | |
| 5,030,210 A | 7/1991 | Alchas | |
| 5,041,089 A | 8/1991 | Mueller et al. | |
| 5,085,630 A | 2/1992 | Osterholm et al. | |
| 5,092,841 A | 3/1992 | Spears | |
| 5,097,829 A * | 3/1992 | Quisenberry | 607/105 |
| 5,106,360 A | 4/1992 | Ishiwara et al. | |
| 5,108,372 A | 4/1992 | Swenson et al. | |
| 5,112,301 A | 5/1992 | Fenton, Jr. et al. | |
| 5,147,385 A | 9/1992 | Beck et al. | |
| 5,149,321 A | 9/1992 | Klatz et al. | |
| 5,151,100 A | 9/1992 | Abele et al. | |
| 5,174,285 A | 12/1992 | Fontenot | |
| 5,180,364 A | 1/1993 | Ginsburg | |
| 5,191,883 A | 3/1993 | Lennox et al. | |
| 5,196,024 A | 3/1993 | Barath | |
| 5,211,631 A | 5/1993 | Sheaff | |
| 5,216,032 A | 6/1993 | Manning | |
| 5,234,405 A | 8/1993 | Klatz et al. | |
| 5,248,312 A | 9/1993 | Langberg | |
| 5,250,070 A | 10/1993 | Parodi | |
| 5,257,977 A | 11/1993 | Eshel | |
| 5,261,399 A | 11/1993 | Klatz et al. | |
| 5,269,758 A | 12/1993 | Taheri | |
| 5,334,181 A | 8/1994 | Rubinsky et al. | |
| 5,342,301 A | 8/1994 | Saab | |
| 5,344,436 A | 9/1994 | Fontenot et al. | |
| 5,368,591 A | 11/1994 | Lennox et al. | |
| 5,395,314 A | 3/1995 | Klatz et al. | |
| 5,403,281 A | 4/1995 | O'Neill et al. | |
| 5,437,633 A | 8/1995 | Manning | |
| 5,437,673 A | 8/1995 | Baust et al. | |
| 5,486,208 A | 1/1996 | Ginsburg | |
| 5,514,094 A | 5/1996 | Anello et al. | |
| 5,531,776 A | 7/1996 | Ward et al. | |
| 5,563,584 A | 10/1996 | Rader et al. | |
| 5,584,804 A | 12/1996 | Klatz et al. | |
| 5,624,392 A | 4/1997 | Saab | |
| 5,645,531 A | 7/1997 | Thompson et al. | |
| 5,653,692 A | 8/1997 | Masterson et al. | |
| 5,676,691 A | 10/1997 | Friedman | |
| 5,678,570 A | 10/1997 | Manning | |
| 5,716,386 A | 2/1998 | Ward et al. | |
| 5,733,319 A | 3/1998 | Neilson et al. | |
| 5,837,003 A | 11/1998 | Ginsburg | |
| 5,871,526 A * | 2/1999 | Gibbs et al. | 607/104 |
| 5,957,963 A | 9/1999 | Dobak, III | |
| 5,965,089 A | 10/1999 | Jarvik et al. | |
| 5,972,013 A | 10/1999 | Schmidt | |
| 5,980,561 A | 11/1999 | Kolen et al. | |
| 6,019,783 A | 2/2000 | Philips et al. | |
| 6,042,559 A | 3/2000 | Dobak, III | |
| 6,051,019 A | 4/2000 | Dobak, III | |
| 6,096,068 A | 8/2000 | Dobak, III et al. | |
| 6,126,684 A | 10/2000 | Gobin et al. | |
| 6,146,411 A * | 11/2000 | Noda et al. | 607/105 |
| 6,149,670 A | 11/2000 | Worthen et al. | |
| 6,149,676 A | 11/2000 | Ginsburg | |
| 6,149,677 A | 11/2000 | Dobak, III | |
| 6,206,004 B1 | 3/2001 | Schmidt et al. | |
| 6,224,624 B1 | 5/2001 | Lasheras et al. | |
| 6,231,594 B1 | 5/2001 | Dae | |
| 6,231,595 B1 | 5/2001 | Dobak, III | |
| 6,235,048 B1 | 5/2001 | Dobak, III | |
| 6,245,095 B1 | 6/2001 | Dobak, III et al. | |
| 6,251,129 B1 | 6/2001 | Dobak, III et al. | |
| 6,254,626 B1 | 7/2001 | Dobak, III et al. | |
| 6,261,312 B1 | 7/2001 | Dobak, III et al. | |
| 6,287,326 B1 | 9/2001 | Pecor | |
| 6,290,717 B1 | 9/2001 | Philips | |
| 6,299,599 B1 | 10/2001 | Pham et al. | |
| 6,312,452 B1 | 11/2001 | Dobak, III et al. | |
| 6,338,727 B1 | 1/2002 | Noda et al. | |
| 6,375,674 B1 | 4/2002 | Carson | |
| 6,607,517 B1 * | 8/2003 | Dae et al. | 604/500 |
| 7,077,825 B1 * | 7/2006 | Stull | 604/113 |
| 7,896,009 B2 * | 3/2011 | Stull | 128/898 |
| 2003/0135252 A1 * | 7/2003 | MacHold et al. | 607/106 |
| 2004/0267340 A1 | 12/2004 | Cioanta et al. | |
| 2005/0028551 A1 | 2/2005 | Noda et al. | |
| 2006/0293732 A1 * | 12/2006 | Collins et al. | 607/104 |
| 2006/0293734 A1 | 12/2006 | Scott et al. | |
| 2007/0043409 A1 * | 2/2007 | Brian et al. | 607/105 |
| 2007/0198072 A1 * | 8/2007 | Montain et al. | 607/108 |
| 2007/0203552 A1 * | 8/2007 | Machold et al. | 607/104 |
| 2007/0244531 A1 * | 10/2007 | Noda et al. | 607/105 |
| 2009/0043366 A1 * | 2/2009 | Dae | 607/113 |
| 2009/0247963 A1 * | 10/2009 | Bleam et al. | 604/246 |

FOREIGN PATENT DOCUMENTS

| | | |
|---|---|---|
| AU | 772661 B2 | 5/2004 |
| WO | 9105528 A1 | 5/1991 |
| WO | 9417842 A1 | 8/1994 |
| WO | 9739707 A1 | 10/1997 |
| WO | 00/09054 A1 | 2/2000 |
| WO | 0010494 A1 | 3/2000 |
| WO | 0038601 A1 | 7/2000 |
| WO | 00/48670 A1 | 8/2000 |
| WO | 00/66053 A1 | 11/2000 |

OTHER PUBLICATIONS

White, R. et al., "Profound selective, cooling and ischemic of primate brain without pump or oxygenator," Surgery, Jul. 1969, pp. 224-232, vol. 66, No. 1.

Weale, F.E., "The Aneroid Manometer in Peripheral Arterial Surgery," The British Journal of Surgery, Aug. 1969, pp. 612-613, 630-631, vol. 56, No. 8.

(56) References Cited

OTHER PUBLICATIONS

Negrin, Jr., J., "The Hypothermostat, An Instrument to Obtain Local Hypothermia of the Brain or Spinal Cord," International Surgery, Aug. 1970, pp. 2, 93-106, Section 1, vol. 54, No. 2.
Safar, P. et al., "Resuscitation after global brain ischemic-anoxia," Critical Care Medicine, Jul.-Aug. 1978, pp. 215-227, vol. 6, No. 4.
Ping, F.C. et al., "Protection of the Brain From Hypoxia: A Review," Canadian Anaesthetists ' Society Journal, Nov. 1978, pp. 468-473, vol. 25, No. 6.
Safar, P., "Dynamics of Brain Resuscitation After Ischemic Anoxia," Hospital Practice, Feb. 1981, pp. 67-72.
Gisvold, S. et al., "Multifaceted Therapy After Global Brain Ischemia in Monkeys," Stroke, Sep.-Oct. 1984, pp. 803-812, vol. 15, No. 5.
Leonov, Y. et al., "Mild Cerebral Hypothermia during and after Cardiac Arrest Improves Neurologic Outcome in Dogs," Journal of Cerebral Blood Flow and Metabolism, (1990), pp. 57-70, vol. 10, No. 1.
Minamisawa, H. et al., "The Effect of Mild Hyperthermia and Hypothermia on Brain Damage Following, 5, 10, and 15 Minutes of Forebrain Ischemia," American Neurological Association, Jul. 1990, pp. 26-33, vol. 28, No. 1.
Tisherman, S. et al., "Therapeutic Deep Hypothermic Circulatory Arrest in Dogs: A Resuscitation Modality for Hemorrahagic Shock with 'Irreparable' Injury," The Journal of Trauma, Jul. 1990, pp. 836-847, vol. 30. No. 7.
Tisherman, S. et al., "Deep Hypothermic Circulatory Arrest Induced During Hemorrhagic Shock in Dogs: Preliminary Systemic and Cerebral Metabolism Studies," Current Surgery, Sep.-Oct. 1990, pp. 327-330.
Leonov, Y. et al., "Moderate Hypothermia After Cardiac Arrest of 17 Minutes in Dogs: Effect on Cerebral and Cardiac Outcome," Stroke, Nov. 1990, pp. 1600-1606, vol. 21, No. 11.
Sterz, F. et al., "Mild Hypothermic Cardiopulmonary Resuscitation Improves Outcome after Prolonged Cardiac Arrest in Dogs," Critical Care Medicine, Mar. 1991, pp. 379-389, vol. 19, No. 3.
Tisherman, S. et al., "Profound Hypothermia (<10.degree. C.) Compared with Deep Hypothermia (15.degree. C.) Improves Neurologic Outcome in Dogs After Two Hours' Circulatory Arrest Induced to Enable Resuscitative Surgery," The Journal of Trauma, Aug. 1991, pp. 1051-1062, vol. 31, No. 8.
Dietrich, W., "The Importance of Brain Temperature in Cerebral Injury," Journal of Neurotrauma, (1992), pp. S475-S485, Supplement 2.
Ginsberg, M. et al., "Therapeutic Modulation of Brain Temperature: Relevance to Ischemic Brain Injury," Cerebrovascular and Brain Metabolism Reviews, (1992), pp. 189-225, vol. 4, No. 3.
Martinez-Arizala, A. et al., "Hypothermia in Spinal Cord Injury," Journal of Neurotrauma, May 1992, pp. S497-S505, vol. 9, Suppl. 2.
Weinrauch, V. et al., "Beneficial Effect of Mild Hypothermia and Detrimental Effect of Deep Hypothermia After Cardiac Arrest in Dogs," Stroke, Oct. 1992, pp. 1454-1462, vol. 23, No. 10.
Kuboyama, K. et al., "Delay in cooling negates the beneficial effect of mild resuscitative cerebral hypothermia after cardiac arrest in dogs: A prospective, randomized study," Critical Care Medicine, Sep. 1993, pp. 1348-1358, vol. 21, No. 9.
Maher, J. et al., "Hypothermia as a Potential Treatment for Cerebral Ischemia," Cerebrovascular and Brain Metabolism Reviews, Sep. 1993, pp. 277-300, vol. 5, No. 4.
Safar, P., "Cerebral Resuscitation After Cardiac Arrest: Research Initiatives and Future Directions," Annals of Emergency Medicine, Feb. 1993, pp. 324-389, vol. 22, No. 2, Part 2.
Oku, K. et al., "Mild Hypothermia After Cardiac Arrest in Dogs Does Not Affect Postarrest Multifocal Cerebral Hypoperfusion," Stroke, Oct. 1993, pp. 1590-1597, vol. 24, No. 10.
Kuboyama, K. et al., "Mild hypothermia after cardiac arrest in dogs does not affect postarrest cerebral oxygen uptake/delivery mismatching," Resuscitation 27, (1994), pp. 231-244.

Laptook, A. et al., "Modest Hypothermia Provides Partial Neuroprotection for Ischemic Neonatal Brain," Pediatric Research, (1994), pp. 436-442, vol. 35, No. 4.
Onoe, M. et al., "The effect of pulsatile perfusion on cerebral blood flow during profound hypothermia with total circulatory arrest," Journal of Thoracic and Cardiovascular Surgery, Jul. 1994, pp. 119-125, vol. 108.
Xiao, F. et al., "Peritoneal cooling for mild cerebral hypothermia after cardiac arrest in dogs," Resuscitation 30, (1995), pp. 51-59.
Sessler, D., "Deliberate Mild Hypothermia," Journal of Neurosurgical Anesthesiology, Jan. 1995, pp. 38-46, vol. 7, No. 1.
Capone, A. et al., "Complete Recovery after Normothermic Hemorrahagic Shock and Profound Hypothermic Circulatory Arrest of 60 Minutes in Dogs," The Journal of Trauma: Injury, Infection, and Critical Care, Mar. 1996, pp. 388-395, vol. 40, No. 3.
Gisvold, S. et al., "Cerebral resuscitation from cardiac arrest: Treatment potentials," Critical Care Medicine, (1996), pp. S69-S80, vol. 24, No. 2 (Suppl.).
Kataoka, K. et al., "Ischemic Neuronal Damge: How Does Mild Hypothermia Modulate It?", Molecular and Chemical Neuropathology, (1996), pp. 191-195, vol. 28.
Safar, F. et al., "Selective brain cooling after cardiac arest," Critical Care Medicine, (1996), pp. 911-914, vol. 24, No. 6.
Sterz, F. et al., "Mild Resuscitative Hypothermia and Outcome After Cardiopuliminary Resuscitation," Journal of Neurosurgical Anesthesiology, Jan. 1996, pp. 88-96, vol. 8, No. 1.
Wass, C. et al., Hypothermia-associated Protection from Ischemic Brain Injury: Implications for Patient Management., International Anesthesiology Clinics: Topics of Neuroanesthesia, Fall 1996, pp. 95-111, vol. 34, No. 4.
Safar, P. et al., "Improved Cerebral Resuscitation From Cardiac Arrest in Dogs With Mild Hypothermia Plus Blood Flow Promotion," Stroke, Jan. 1996, pp. 105-113, vol. 27, No. 1.
Marion, D. et al., "Resuscitative hypothermia," Critical Care Medicine, Feb. 1996, pp. S81-S89, vol. 24, No. 2 (Suppl.).
Rosomoff, H. et al., "Resuscitation from severe brain trauma," Critical Care Medicine, Feb. 1996, pp. S48-S56, vol. 24, No. 2 (Suppl.).
Markarian, G. et al., "Mild Hypothermia: Therapeutic Window After Experimental Cerebral Ischemia," Neurosurgery, Mar. 1996, pp. 542-551, vol. 38, No. 3.
Hoffman, W. et al., "Effects of graded hypothermia on outcome from brain ischemic," Neurological Research, Apr. 1976, pp. 185-189, vol. 18, No. 2.
Schwartz, A. et al., "Isolated Cerebral Hypothermia by Single Carotid Artery Perfusion of Extracorporeally Cooled Blood in Baboons," Neurosurgery, Sep. 1996, pp. 577-582, vol. 39, No. 3.
Metz, C. et al., "Moderate hypothermia in patients with severe head injury: cerebral and extracerebral effects," Journal of Neurosurgery, Oct. 1996, pp. 533-541, vol. 85, No. 4.
Barone, F. et al., "Brain Cooling During Transient Focal Ischemia Provides Complete Neuroprotection," Neuroscience and Biobehavioral Reviews, (1997), pp. 31-44, vol. 21, No. 1.
Tisherman, S. et al., "Future directions for resuscitation research. V. Ultra-advanced life support," Resuscitation 34, (1997), pp. 281-293.
Colbourne, F. et al., "Postischemic Hypothermia: A Critical Appraisal with Implications for Clinical Treatment," Molecular Neurobiology, Jun. 1997, pp. 171-201, vol. 14, No. 3.
Nesbit, G. et al., "Intracranial intraarterial thrombolysis facilitated by microcatheter navigation through an occluded cervical internal carotid artery," Journal Neurosurgery, Mar. 1996, pp. 387-392, vol. 84.
European Patent Office Search Report dated Jul. 20, 2007.
PCT International Search Report for PCT/2013/071527 filed Nov. 22, 2013.

* cited by examiner

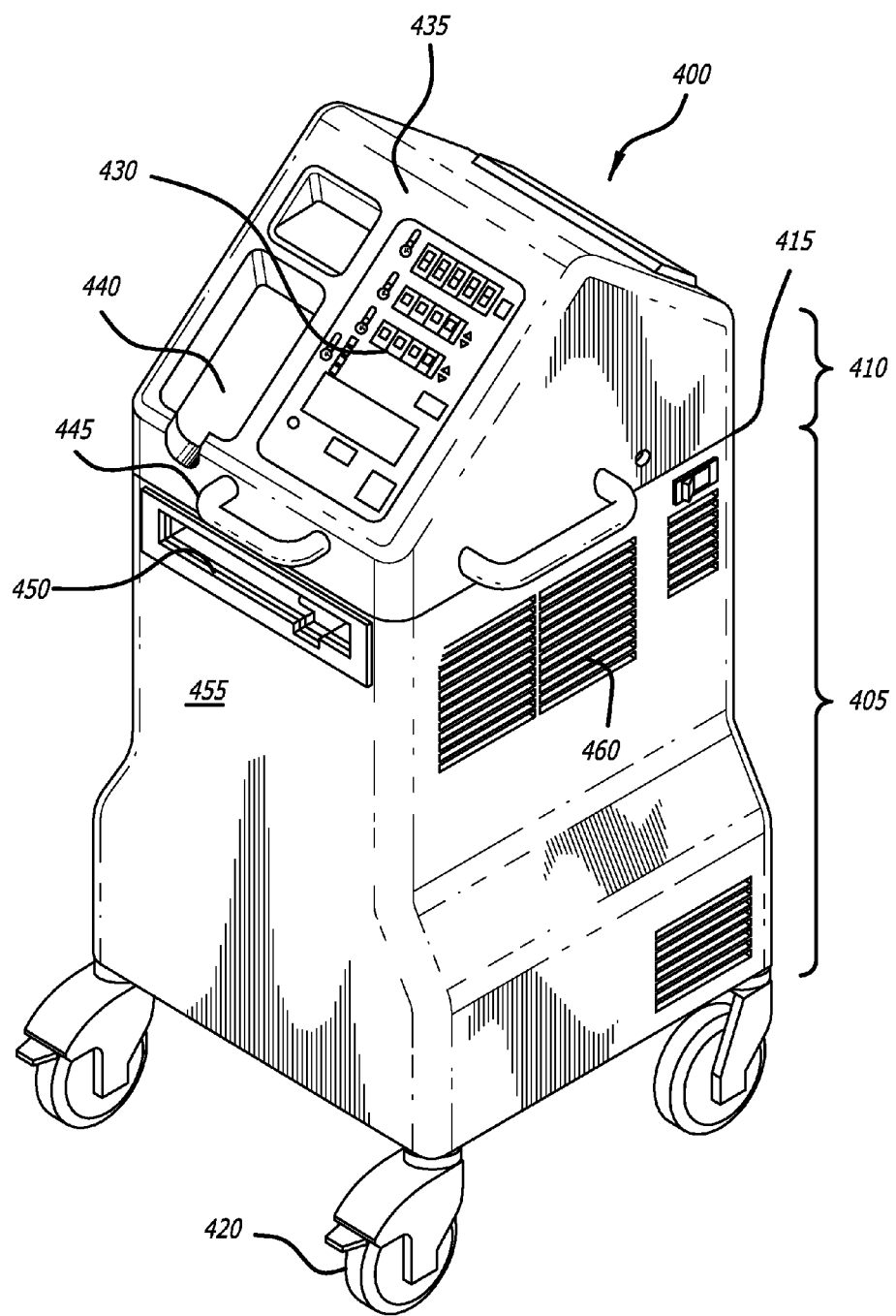

SYSTEM AND METHOD FOR MANAGEMENT OF BODY TEMPERATURE

BACKGROUND

1. Field of the Invention

The present invention relates generally to medical devices and methods and, more particularly, to a programmable, microprocessor based system and method for controlling the temperature and flow of a thermal exchange fluid that is circulated through a heat exchange catheter inserted into a patient's body for the purpose of cooling or warming at least a portion of the patient's body.

2. Background of the Invention

Under ordinary circumstances, the thermoregulatory mechanisms of a healthy human body serve to maintain the body at a constant temperature of about 37° C. (98.6° F.), a condition sometimes referred to as normothermia. To maintain normothermia, the thermoregulatory mechanisms act so that heat lost from the person's body is replaced by the same amount of heat generated by metabolic activity within the body. For various reasons such as extreme environmental exposure to a cold environment or loss of thermoregulatory ability as a result of disease or anesthesia, a person may develop a body temperature that is below normal, a condition known as hypothermia. A person may develop a condition that is above normothermia, a condition known as hyperthermia, as a result of extreme exposure to a hot environment, or malfunctioning thermoregulatory mechanisms, the latter being a condition sometimes called malignant hyperthermia. The body may also establish a set point temperature (that is, the temperature which the body's thermoregulatory mechanisms function to maintain) that is above normothermia, a condition usually referred to as fever. The present invention addresses all of these situations.

Accidental hypothermia is generally a dangerous condition that may even be life threatening, and requires treatment. If severe, for example where the body temperature drops below 30° C., hypothermia may have serious consequences such as cardiac arrhythmias, inability of the blood to clot normally, or interference with normal metabolism. If the period of hypothermia is extensive, the patient may even experience impaired immune response and increased incidence of infection.

Simple methods for treating accidental hypothermia have been known since very early times. Such methods include wrapping the patient in blankets, administering warm fluids by mouth, and immersing the patient in a warm water bath. If the hypothermia is not too severe, these methods may be effective. However, wrapping a patient in a blanket depends on the ability of the patient's own body to generate heat to re-warm the body. Administering warm fluids by mouth relies on the patient's ability to swallow, and is limited in the temperature of the liquid consumed and the amount of fluid that may be administered in a limited period of time. Immersing a patient in warm water is often impractical, particularly if the patient is simultaneously undergoing surgery or some other medical procedure.

More recently, hypothermia may be treated in a more complex fashion. Heated warming blankets may be applied to a patient or warming lamps that apply heat to the skin of the patient may be used. Heat applied to the patient's skin, however, has to transmit through the skin by conduction or radiation which may be slow and inefficient, and the blood flow to the skin may be shut down by the body's thermoregulatory response, and thus, even if the skin is warmed, such mechanisms may be ineffective in providing heat to the core of the patient's body. When breathing gases are administered to a patient, for example a patient under anesthesia, the breathing gases may be warmed. This provides heat relatively fast to the patient, but the amount of heat that can be administered without injuring the patient's lungs is very limited. An alternative method of warming a hypothermic patient involves infusing a hot liquid into the patient via an IV infusion, but this is limited by the amount of liquid that can be infused and the temperature of the liquid.

In extreme situations, a very invasive method may be employed to control hypothermia. Shunts may be placed into the patient to direct blood from the patient through an external machine such as a cardiopulmonary by-pass (CPB) machine which includes a heater. In this way, the blood may be removed from the patient, heated externally, and pumped back into the patient. Such extreme measures have obvious advantages as to effectiveness, but also obvious drawbacks as to invasiveness. The pumping of blood through an external circuit that treats the blood is generally quite damaging to the blood, and the procedure is only possible in a hospital setting with highly trained personnel operating the equipment.

Accidental hyperthermia may also result from various conditions. Where the normal thermoregulatory ability of the body is lost, because of disease or anesthesia, run-away hyperthermia, also known as malignant hyperthermia, may result. The body may also set a higher than normal set point resulting in fever which is a type of hyperthermia. Like hypothermia, accidental hyperthermia is a serious condition that may sometimes be fatal. In particular, hyperthermia has been found to be neurodestructive, both in itself or in conjunction with other health problems such as traumatic brain injury or stroke, where a body temperature in excess of normal has been shown to result in dramatically worse outcomes, even death.

As with hypothermia, when the condition is not too severe, simple methods for treating the condition exist, such as cold water baths and cooling blankets, or antipyretic drugs such as aspirin or acetaminophen, and for the more extreme cases, more effective but complex and invasive means such as cooled breathing gases, cold infusions, and blood cooled during CPB also exist. These, however, are subject to the limitations and complications as described above in connection with hypothermia.

Although both hypothermia and hyperthermia may be harmful and require treatment in some case, in other cases hyperthermia, and especially hypothermia, may be therapeutic or otherwise advantageous, and therefore may be intentionally induced. For example, periods of cardiac arrest or cardiac insufficiency in heart surgery result in insufficient blood to the brain and spinal cord, and thus can produce brain damage or other nerve damage. Hypothermia is recognized in the medical community as an accepted neuroprotectant and therefore a patient is often kept in a state of induced hypothermia while undergoing treatment for the underlying cause of the condition. Hypothermia also has similar advantageous protective ability for treating or minimizing the adverse effects of certain neurological diseases or disorders such as head trauma, spinal trauma and hemorrhagic or ischemic stroke. Therefore it is sometimes desirable to induce whole-body or regional hypothermia for the purpose of facilitating or minimizing adverse effects of certain surgical or interventional procedures such as open heart surgery, aneurysm repair surgeries, endovascular aneurysm repair procedures, spinal surgeries, or other surgeries where blood flow to the brain, spinal cord or vital organs may be interrupted or compromised. Hypothermia has even been found to be advantageous to protect cardiac muscle tissue after a myocardial infarct (MI).

Current methods of attempting to induce hypothermia generally involve constant surface cooling, by cooling blanket or by alcohol or ice water rubs. However, such cooling methods are extremely cumbersome, and generally ineffective to cool the body's core. The body's response to cold alcohol or ice water applied to the surface is to shut down the circulation of blood through the capillary beds, and to the surface of the body generally, and thus to prevent the cold surface from cooling the core. If the surface cooling works at all, it does so very slowly. There is also an inability to precisely control the temperature of the patient by this method.

If the patient is in a surgical setting, the patient may be anesthetized and cooled by CPB as described above. Generally, however, this is only available in the most extreme situations involving a full surgical team and full surgical suite, and importantly, is only available for a short period of time because of the damage to the blood caused by pumping. Generally surgeons do not wish to pump the blood for periods longer than four hours, and in the case of stroke or traumatic brain damage, it may be desirable to induce hypothermia for longer than a full day. Because of the direct control of the temperature of a large amount of blood, this method allows fairly precise control of the patient's temperature. However, it is this very external manipulation of large amounts of the patient's blood that makes long term use of this procedure very undesirable.

Means for effectively adding heat to the core of the body that do not involve pumping the blood with an external, mechanical pump have been suggested. For example, a method of treating hypothermia or hyperthermia by means of a heat exchange catheter placed in the bloodstream of a patient was described in U.S. Pat. No. 5,486,208 to Ginsburg, the complete disclosure of which is incorporated herein by reference. Means of controlling the temperature of a patient by controlling such a system is disclosed in U.S. Pat. No. 5,837,003, also to Ginsburg, the complete disclosure of which is incorporated herein by reference. A further system for such controlled intravascular temperature control is disclosed in publication WO 00/10494 to Ginsburg et al., the complete disclosure of which is incorporated herein by reference. Those patents and publication disclose a method of treating or inducing hypothermia by inserting a heat exchange catheter having a heat exchange area including a balloon with heat exchange fins into the bloodstream of a patient, and circulating heat exchange fluid through the balloon while the balloon is in contact with the blood to add or remove heat from the bloodstream. (As used herein, a balloon is a structure that is readily inflated under pressure and which collapses when the pressure is reduced.)

A number of catheter systems for cooling tissue adjacent the catheter or regulating the temperature of the catheter using the temperature of fluid circulating within the catheter are shown in the published art. Some such catheters rely on a reservoir or similar tank for a supply of heat exchange fluid. For such systems that involve a catheter placed in the bloodstream, however, difficulties arise in sterilizing the fluid source between uses and rapidly changing the temperature of a large volume of fluid having a significant thermal mass.

Various approaches have been used to add or remove heat the heat exchange fluid that is circulated through the catheter. For example, the heat exchange fluid may be circulated through a bath containing a second heat exchange fluid, such as a glycol based heat exchange fluid, water, or the like. Another approach uses a refrigeration system to either directly or indirectly cool the circulating heat exchange fluid. Yet another approach employs a thermoelectric system for heating and cooling the circulating heat exchange fluid.

Each of the systems mentioned above have their own advantages and disadvantages. For example, in some circumstances, such as in an emergent cardiac arrest, it has been found beneficial to rapidly reduce the patient's temperature. Such a rapid temperature reduction requires a large amount of cooling power, which results in the need for a refrigeration unit that produces a higher than acceptable noise level. Once a patient's temperature has been reduced to the desired level, however, less cooling power is required to maintain the patient at the desired temperature. In such situations, a thermoelectric cooler is preferable, because of the fine control over the temperature of the circulating fluid that can be maintained using such a system.

For the foregoing reasons, there is a need for a rapid and effective means to add or remove heat from the heat exchange fluid circulating through a catheter used to control the body temperature of a patient in an effective and efficient manner, while avoiding the inadequacies of the prior art methods. Such a system would provide large amounts of cooling power to rapidly reduce the patient's temperature to a desired level, yet would also provide accurate control of the heat removed from the patient to maintain the patient at the desired level without undesirable over- or under-shoot of the patient's temperature. The present invention satisfies these and other needs.

SUMMARY OF THE INVENTION

In it most general aspect, the present invention provides a system for providing large amounts of cooling power to remove heat from a heat exchange fluid that is circulating between an external heat exchanger and an intravascular heat exchange catheter inserted into the vasculature of a patient. In this general aspect, the system includes a first stage that capable of providing high cooling power using a refrigeration system utilizing a compressible fluid or gas. The second state of the system provides for more fine control of the rate of heat removal, or cooling provided to the heat exchange fluid. In one aspect, both stages may be used in concert to provide maximal cooling. In another aspect, the first stage may be de-activated when a sensed temperature related to the temperature of a patient indicates that the temperature of the patient is equal to or lower than a threshold temperature close to a target temperature has been achieved, with the second stage providing cooling until the target temperature is reached. In yet another aspect, the second stage may is also capable of providing heat to the heat exchange fluid when necessary to maintain a sensed temperature at the target temperature or to warm a patient.

In another general aspect, the present invention provides a controller that controls the operation of the stages of the heater/cooler device to provide accurate control of the rate of heating or cooling of a patient, or to maintain the temperature of a patient at a target temperature.

In another aspect, the present invention includes a system for managing the temperature of a person using an intravascular heat exchanger inserted into the lumen of a body vessel of a patient, comprising: an intravascular heat exchanger having a fluid input port and a fluid output port; an external heat exchanger having an input and an output port, the input and output ports, the intravascular heat exchanger and the external heat exchanger forming a fluid circuit; a pump disposed within the fluid circuit for pumping heat exchange fluid through the fluid circuit; a heater/cooler configured to engage the external heat exchanger in a thermal transfer relationship, the heater/cooler including a primary cooling portion and a reversible secondary portion capable of heating or cooling, the primary cooling portion including a refrigeration circuit including a compressor, a condenser, an expansion valve, and a cold block in thermal communication with the reversible secondary portion; and a controller having a processor configured by software commands to receive temperature indications related to the temperature of a patient and to control operation of the heater/cooler in accordance with a target temperature.

In still another aspect, the fluid input and the fluid output of the intravascular heat exchanger each have releasable couplings, and wherein the input and output ports of the external heat exchanger have releasable couplings, the releasable coupling of the input port configured to engage the releasable coupling disposed on the fluid output of the intravascular heat exchanger and the releasable coupling of the output port configured to engage the releasable coupling of the fluid input of the intravascular heat exchanger.

In yet another aspect, the reversible secondary portion is a T/E cooler.

In still another aspect, the controller activates the primary cooling portion to remove heat from the heat exchange fluid when the difference between the sensed patient temperature and the target temperature exceeds a selected value. In an alternative aspect, the controller activates the primary cooling portion and the reversible secondary portion to remove heat from the heat exchange fluid when the difference between the sensed patient temperature and the target temperature exceeds a selected value. In yet another alternative aspect, the controller activates the reversible secondary portion to remove heat from the heat exchange fluid when the difference between the sensed patient temperature and the target temperature is less than a selected value. In still another alternative aspect, the controller activates the reversible secondary portion to add heat to the heat exchange fluid when the sensed patent temperature is less than the target temperature.

In another aspect, the controller deactivates the primary cooling portion and activates the reversible secondary portion when the difference between the sensed patient temperature and the target temperature is less than a selected value. In an alternative aspect, the controller deactivates the primary cooling portion when the difference between the sensed patient temperature and the target temperature is less than a selected value.

In a further aspect, the present invention includes a communication module configured to communicate information related to the sensed temperature and the operation of the system to a display remote from the system. In an alternative aspect, the communication module is configured to communicate information related to the sensed temperature and the operation of the system to a data management system. In another aspect, the information communicated to the data management system is associated with an electronic medical record of the patient.

In still another aspect, the present invention includes a communication module configured to communicate with a device monitoring a health parameter of the patient; and a display controlled by the processor of the controller to display information related to the operation of the system and information received from the monitoring device related to the monitored health parameter of the patient.

In yet another aspect, the present invention includes a secondary cooling circuit disposed between the refrigeration circuit and the fluid circuit, the secondary cooling circuit comprising a pump for pumping secondary heat exchange fluid through the secondary cooling circuit, a secondary cold block configured to engage the cold block of the refrigeration circuit in a heat exchange configuration, and a third cold block configured to engage the external heat exchanger of the fluid circuit in a heat exchange configuration. In one alternative aspect, the reversible secondary portion of the heater cooler is disposed in the secondary cooling circuit rather than the primary cooling circuit. In another alternative aspect, the third block is a container having an input and an output, the container configured to receive the external heat exchanger such that the external heat exchanger is immersed in the secondary heat exchange fluid flowing through the container.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 7A is a perspective view of an exemplary re-usable control unit of the present invention;

DETAILED DESCRIPTION OF THE EMBODIMENTS

Figure 1:
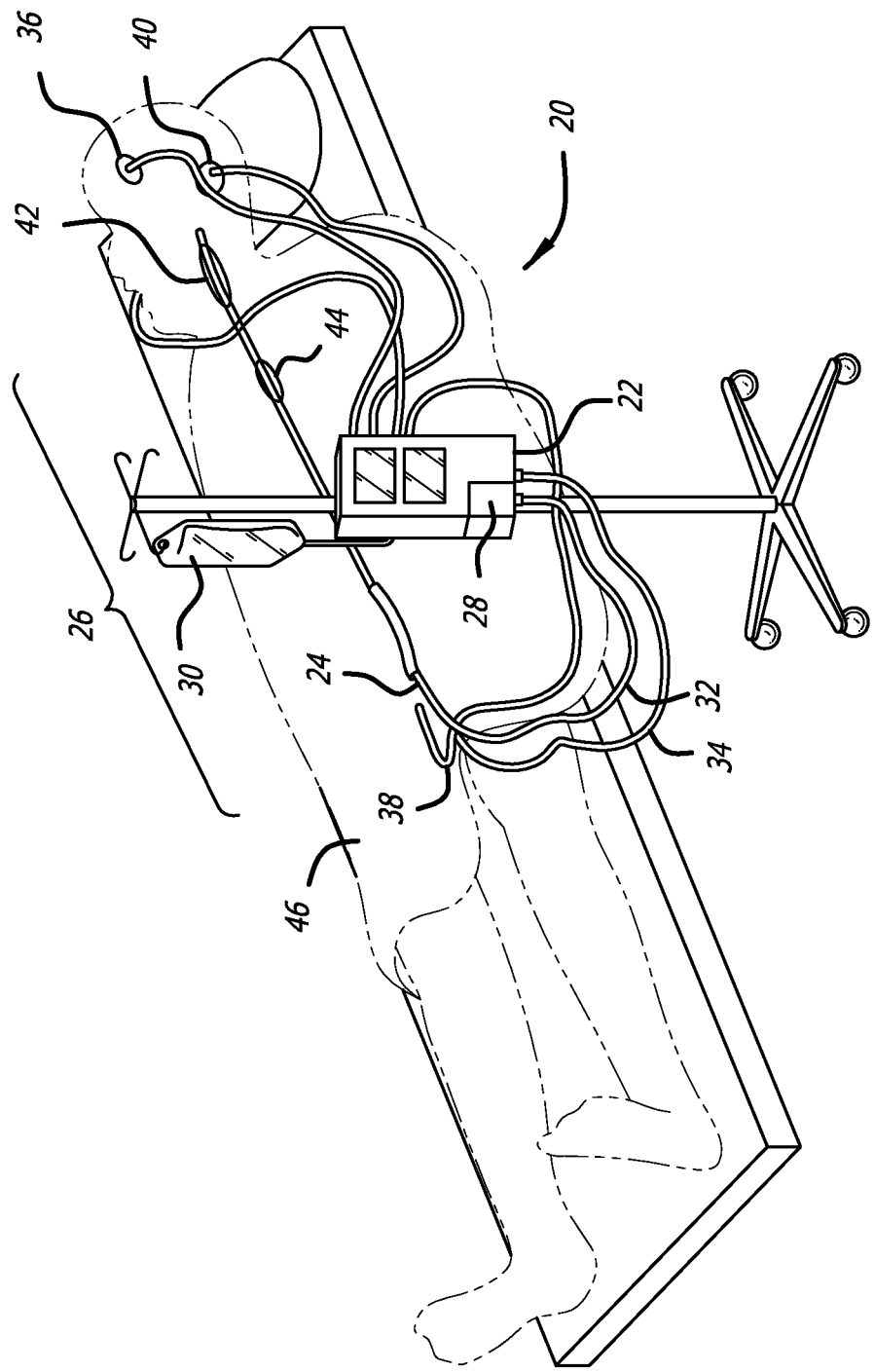
FIG. 1 is a perspective view of a patient undergoing treatment using a system in accordance with the present invention.

The present invention is primarily intended to include a catheter placed in the bloodstream of a patient for regulating the patient's body temperature, although those skilled in the art will understand that various other applications for the system of the present invention are possible. Indeed, the present invention may have applications beyond controlling the temperature of an internal body fluid and the claims should not be so limited.

In a preferred application; one or more of the heat exchange catheters of the present invention are positioned within a patient's vasculature to exchange heat with the blood in order to regulate the overall body temperature or to regulate the temperature of a localized region of the patient's body. Heat exchange fluid is then circulated through the catheter to exchange heat between the blood and the heat exchange fluid; and a controller manages the functioning of the system. The catheters may be, for example, suitable for exchanging heat with blood flowing toward the brain to cool the brain, and may thus prevent damage to brain tissue that might otherwise result from a stroke or other injury; or cooling blood flowing toward the heart to cool the myocardium to prevent tissue injury that might otherwise occur following an MI or other similar event.

In general the invention provides a control unit and method for controlling the temperature and flow of heat exchange fluid for a heat exchange catheter used for controlling the body temperature of a patient. The control unit initially automatically supplies heat exchange fluid to the heat exchange catheter to prime the heat exchange catheter for use. It also receives input from the user regarding control parameters that are used to control the operation of the system. Additionally the controller also receives temperature information from sensors that sense patient temperature information; and based thereon, automatically controls the temperature of the heat exchange fluid by controlling the various embodiments of heater/cooling systems used to add heat to or remove heat from the heat exchange fluid. The controller also monitors the operation of the system, including various parameters associated with the temperature, level and flow of the heat exchange fluid and is programmed to providing various warning or alarm states that may warn the user of dangerous situations, for example, by shutting down the pump motor and notifying the user if the fluid level in the system is unacceptably low.

Overview of Heat Exchange System

Any suitable heat exchange catheter may be utilized in a heat exchange system for regulating the temperature of a patient or a region of the patient's body and controlled by the control unit as disclosed herein. In addition to the catheters disclosed herein, and by way of illustration and not of limitation; catheters that may be utilized in this invention are the catheters disclosed in U.S. Pat. No. 5,486,208 to Ginsburg, U.S. Pat. No. 5,837,003 to Ginsburg, WO 00/10494 to Ginsburg et al., and U.S. Pat. No. 5,624,392 to Saab, the complete disclosure of each of which is hereby incorporated in full herein by reference.

Referring now to the drawings in detail, in which like reference numerals indicate like or corresponding elements among the several figures, one example of such a heat exchange catheter system 20 is shown in FIG. 1, and includes a control unit 22 and a heat exchange catheter 24 formed with at least one heat transfer section 44. The heat transfer section or sections are located on that portion of the catheter 24, as illustrated by section 26 that is inserted into the patient. This insertion portion is less than the full-length of the catheter and extends from the location on the catheter just inside the patient; when the catheter is fully inserted, to the distal end of the catheter. The control unit 22 may include a fluid pump 28 for circulating a heat exchange fluid or medium within the catheter 24 and a heat exchanger component for heating and/or cooling circulating fluids within the heat transfer system 20.

A reservoir or fluid bag 30 may be connected to the control unit 22 to provide a source of heat exchange fluid such as, saline, blood substitute solution or other biocompatible fluid. A circulatory heat exchange flow channel within the catheter may be respectively connected to inlet 32 and outlet 34 conduits of the pump 28 for circulation of the heat transfer fluid through the balloon to heat or cool the flow of a body fluid such as blood.

The control unit 22 may further receive data from a variety of sensors which may be, for example, solid-state thermocouples or other suitable sensors to provide feedback from the catheter and various sensors to provide patient temperature information representing core temperature or temperature of selected organs or portions of the body. For instance, sensors may include a temperature probe 36 for the brain or head region, a rectal temperature probe 38, an ear temperature probe 40, an esophageal temperature probe (not shown); a bladder temperature probe (not shown) and the like.

Based upon sensed temperatures and conditions, the control unit 22 may direct the heating or cooling of the catheter. The control unit 22 may activate a heat exchanger at a first sensed temperature to heat fluid which is then circulated through the balloon, and may also de-activate the heat exchanger at a second sensed temperature which may be relatively higher or lower than the first sensed temperature or any other predetermined temperature. Alternatively, the control unit may actively cool the heat exchange fluid to cool the balloon. The control unit 22 may operate multiple heat transfer units to independently heat or cool different selected heat transfer sections to attain desired or preselected temperatures in body regions. The controller might also activate or de-activate other apparatus, for example external heating blankets or the like in response to sensed temperatures. For example, a heating blanket of the type using embedded electrical wires may be controlled by the controller. Alternatively, a heating/cooling blanket having embedded fluid tubes for circulation of a heat exchange fluid may also be fluidly connected to the system. In this embodiment, the controller would control the temperature of the heating/cooling blanket in the same manner as a heat exchange catheter.

The regulation exercised over the heat transfer catheters or other devices may be a simple on-off control, or may be a significantly more sophisticated control scheme including regulating the degree of heating or cooling by controlling the amount of heat added to or removed from the heat exchange fluid, ramp rates of heating or cooling of the body or body portion (rate of change of the temperature of the body or body portion), as measured by the temperature sensors, proportional control as the temperature of the heat exchange region or patient approaches a target temperature; or the like.

In one embodiment, the control unit 22 may include a thermoelectric cooler and heater (and associated flow conduits) that are selectively activated to perform both heating and cooling functions with the same or different heat transfer mediums within the closed loop catheter system. For example; a first heat transfer section 42 located on the insertion portion 26 of at least one temperature regulating catheter 24 may circulate a cold solution in the immediate head region; or alternatively, within a carotid artery or other blood vessel leading to the brain. The head temperature may be locally monitored with temperature sensors 36 positioned in a relatively proximate exterior surface of the patient or within selected body regions. Another heat transfer section 44 of the catheter 24 also located on the insertion portion 26 may circulate a heated solution within a collapsible balloon or otherwise provide heat to other body locations through heat elements or other mechanisms described in accordance with other aspects of the invention. While heat exchange catheter 24 may provide regional hypothermia to the brain region for neuroprotective benefits, other parts of the body may be kept relatively warm so that adverse side effects such as discomfort, shivering, blood coagulopathies, immune deficiencies, and the like, may be avoided or minimized. Warming of the body generally below the neck may be further achieved by insulating or wrapping the lower body in a heating pad or blanket 46 while the head region above the neck is cool. It should be understood of course that multiple heat exchange sections of the catheter 24 may be modified to provide whole body cooling or warming to affect body core temperature.

Exemplary heat exchange system

The various embodiments of the present invention contemplates the use of a re-usable controller or control console having a heater/cooler device therein and which receives a disposable heat exchange element coupled via conduits to a distal in-dwelling heat exchange catheter. More specifically, in one embodiment the controller desirably includes an outer housing having an opening or slot for receiving the heat exchange element, the opening and housing ensuring reliable positioning of the heat exchange element in proximity with the heater/cooler device. In this manner, set up of the system is facilitated because the operator only needs to fully insert and seat the heat exchange element into the controller opening in order to couple the reusable and disposable portions of the system.

Figure 2:
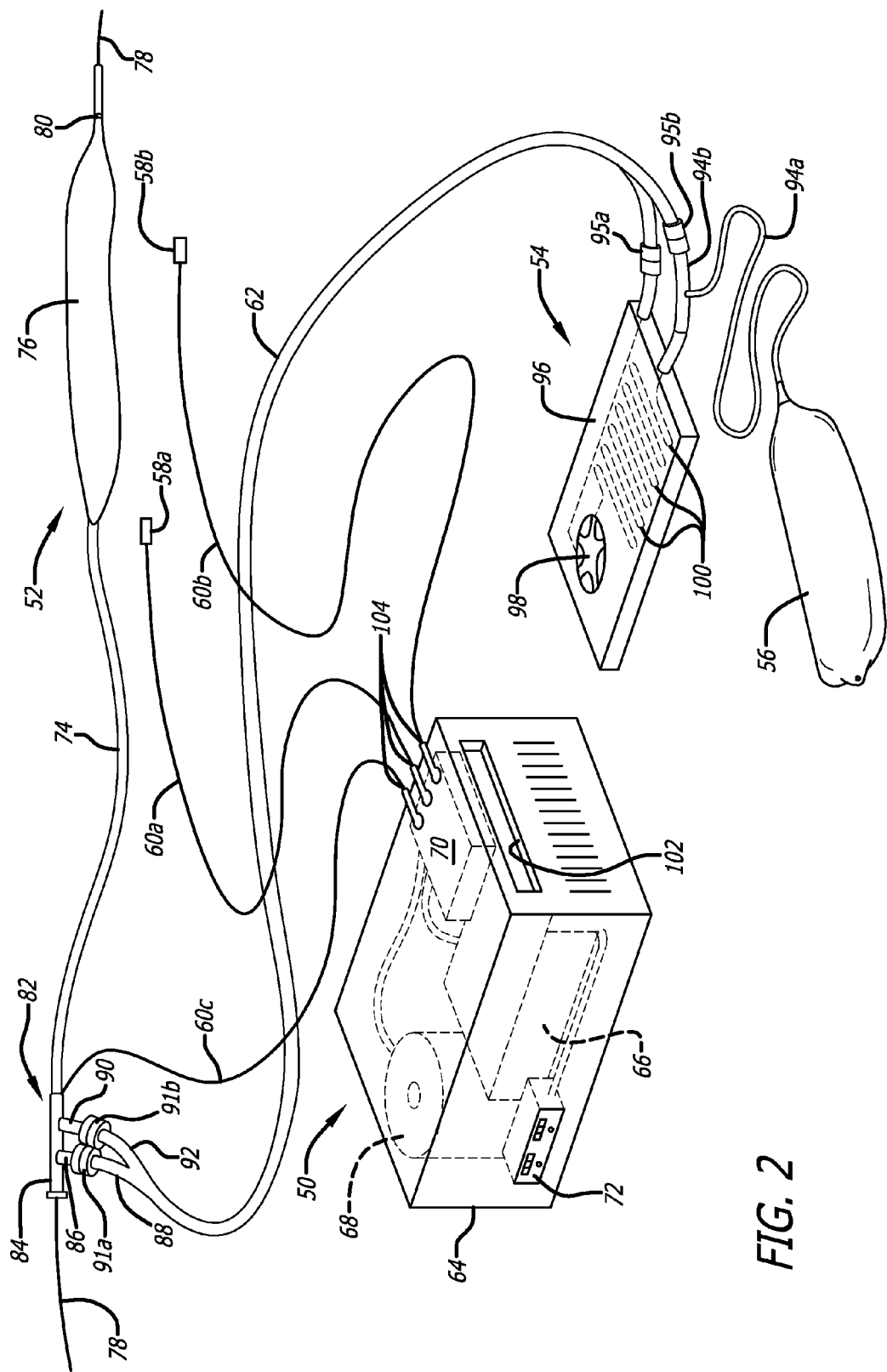
FIG. 2 is a schematic illustration of a disposable heat exchange cassette attached to a heat exchange catheter and an external fluid source; and positioned for insertion into a suitable opening in a re-usable control unit of the present invention.

In an exemplary embodiment, FIG. 2 illustrates a heat exchange catheter system that includes a re-usable control unit 50 and a plurality of disposable components including a heat exchange catheter 52, a heat exchange element 54, a saline bag 56, sensors 58a, 58b and associated wires 60a, 60b, and a plurality of fluid flow conduits including a two-way conduit 62 connecting the heat exchange catheter 52 with the heat exchange element 54. Couplers 95a, 95b may be disposed between heat exchange element 54 and a proximal end of conduit 62, the couplers configured such that conduit 62 is removably connected to heat exchange element 54. Similarly, couplers 91a, 91b may be disposed between heat exchange catheter 52 and a distal end of conduit 62. Thus, depending on the embodiment, conduit 62 may be releasably coupled to the heat exchange catheter 52, the heat exchange element 54, or both. In another embodiment, conduit 62 may not have any couplers. In such an embodiment, the heat exchange catheter 52 and element 54 would be an integral assembly.

The re-usable control unit 50 includes an outer housing 64 within which is provided a heater/cooler 66 a pump driver 68, and a controller processor 70. In addition, a manual input unit 72 enables an operator to enter desirable operating parameters of the controller, for example a pre-selected temperature for the brain. Each of the electronic devices provided within the control unit 50 communicate through suitable wiring.

The heat exchange catheter 52 is formed with a catheter conduit 74 and a heat exchanger 76 which may be, for example, a heat exchange balloon operated using a closed-loop flow of a biocompatible fluid that serves as the heat exchange medium. The catheter 52 may include a working lumen (not shown) for injection of drugs, fluoroscopic dye, or the like, and for receipt of a guidewire 78 for use in placing the catheter at an appropriate location in the patient's body. A sensor 80 may be provided on the catheter 52 distal to the heat exchanger 76 to monitor the temperature of the heat exchange balloon and other sensors (not shown) may be provided as desired to monitor the blood temperature at the distal tip of the catheter; at the proximal tip of the balloon, or at any other desired location along the catheter.

As seen in FIG. 2, the proximal end of the catheter conduit 74 may be connected to a multi-arm adapter 82 for providing separate access to various channels in the catheter 52. For example, a first arm 84 may provide access to the working lumen of the catheter 52 for insertion of the guidewire 78 to steer the heat exchange catheter to the desired location. Where the heat exchanger 76 is a heat exchange balloon for closed-loop flow or a heat exchange medium the adapter 82 may contain a second arm 86 connected to an inflow line 88, and a third arm 90 connected to an outflow line 92. The inflow line 88 and outflow line 92 are therefore placed in flow communication with respective inflow and outflow channels (not shown) provided in the conduit 74 and heat exchanger 76. In this regard, the inflow and outflow lines 88, 92 may come together to form the dual channel conduit 62 connected to the heat exchange element 54. Furthermore, an external fluid source such as the saline bag 56 may be placed in fluid communication with the outflow line 92 via a conduit 94a and a T-junction 94b. As will be explained further below, the external fluid source is used to prime the closed loop heat exchange balloon system. Alternatively, the external fluid source may be directly connected to the heat exchange unit 54.

Still with reference to FIG. 2, the heat exchange unit 54 desirably includes a heat exchange plate 96 and a pump head 98. The pump head 98 pumps heat exchange fluid through a serpentine fluid pathway 100 in the heat exchange plate 96, and through the associated conduits and catheter 52. As mentioned, the heat exchange unit 54 is configured to install into the re-usable control unit 50. In this regard; the heat exchange unit 54 is desirably plate-shaped and sized to fit through art elongate slot 102 in the control unit housing 64. Once inserted, the pump head 98 is placed in proximity to and engaged with the pump driver 68, and the heat exchange plate 96 is placed in proximity to and in thermal communication with the heater/cooler 66. A solid-state thermoelectric heater/cooler 66 is advantageous because the same unit is capable of either generating heat or removing heat by simply changing the polarity of the current activating the unit.

In the embodiment shown, the pump driver 68 engages and activates the pump head 98 to cause it to circulate heat exchange fluid through the heat exchange unit 54 and the serpentine path 100 in the heat exchange plate 96. Therefore, when the heat exchanger unit 54 is properly installed in the control unit 50, the heater/cooler 66 may act to heat or cool the heat exchange fluid as that fluid is circulated through the serpentine pathway 100 and thereafter through the conduits leading to the in-dwelling heat exchanger 76. When the heat exchange fluid is circulated through the heat exchanger 76 located in the patient's body, it may act to add or remove heat from the body. In this way the heater/cooler 66 regulates the blood temperature of the patient as desired.

The heater/cooler 66 and a pump driver 68 are responsive to the controller processor 70. The processor 70 receives data input through electrical connections 104 to numerous sensors, for example body temperature sensors 58a, 58b positioned to sense the temperature at various locations within the patient. For example the temperature may be sensed at the patient's ear, brain region; bladder, rectum, esophagus, or other appropriate location as desired by the operator. Also, as mentioned, a sensor 80 may monitor the temperature of the heat exchanger 76, and other sensors along the catheter 52 may provide input to the controller processor 70, such as via a wire 60c. Additionally, by means of the manual input unit 72, an operator provides the operating parameters of the control system such as, for example; a pre-selected temperature for the brain and/or the whole body of the patient, also called a "target" temperature, a desired rate of heating or cooling (ramp rate). In other embodiments, the operator may input other parameters used to control the operation of the system, such as set point variances, threshold temperatures that are used to change the operation of the system, such as, for example, to reduce the rate of heat removal (cooling) from the heat exchange fluid to control the rate of body temperature change. The operator input parameters are communicated to the controller processor 70 by means of appropriate wiring.

The controller processor 70 coordinates the various data received and selectively actuates the several operational subsystems to achieve and maintain desired results, i.e., proper regulation of the patient's body temperature. For example, the processor 70 may actuate the heater/cooler 66 to increase the amount heat it is removing if the actual temperature is above the specified temperature, or it may decrease the amount of heat being removed if the temperature is below the specified temperature. The heater/cooler may also be controlled to add/remove heat in a controlled fashion to control the rate of temperature change in the patient to achieve a desired rate of change. Alternatively, the processor 70 may stop the pumping of the heat exchange fluid when the sensed body or regional temperature reaches the desired temperature.

Referring still to FIG. 2, the disposable heat exchange unit 54 of the invention is shown as being attached to a heat exchange catheter 52, external fluid source 56 is positioned in cooperation with a suitable reusable control unit. Prior to commencing, treatment the heat exchange unit 54 is inserted into the revisable control unit 50, the external fluid source 56 is attached to the fill port and the pump 98 is automatically or passively primed and the disposable system filled, after which the catheter is ready for insertion in the vasculature of the patient; for example in the inferior vena cava or the carotid artery. Chilled or warmed biocompatible fluid such as saline, is pumped into the carotid artery. Chilled or warmed biocompatible fluid such as saline, is pumped into the closed circuit catheter, which exchanges heat directly with the patient's blood. The control unit serves to automatically control the patient's temperature. Once treatment with the catheter is complete, the catheter is removed from the patient and the cassette is removed from the reusable control unit. Both the catheter and cassette are then discarded. The reusable control unit, however, which never comes into direct contact with the heat exchange fluid, is ready for immediate use for treatment on other patients, along with a new cassette and catheter and fresh external fluid source.

Exemplary Method of Temperature Control

Figure 3A:
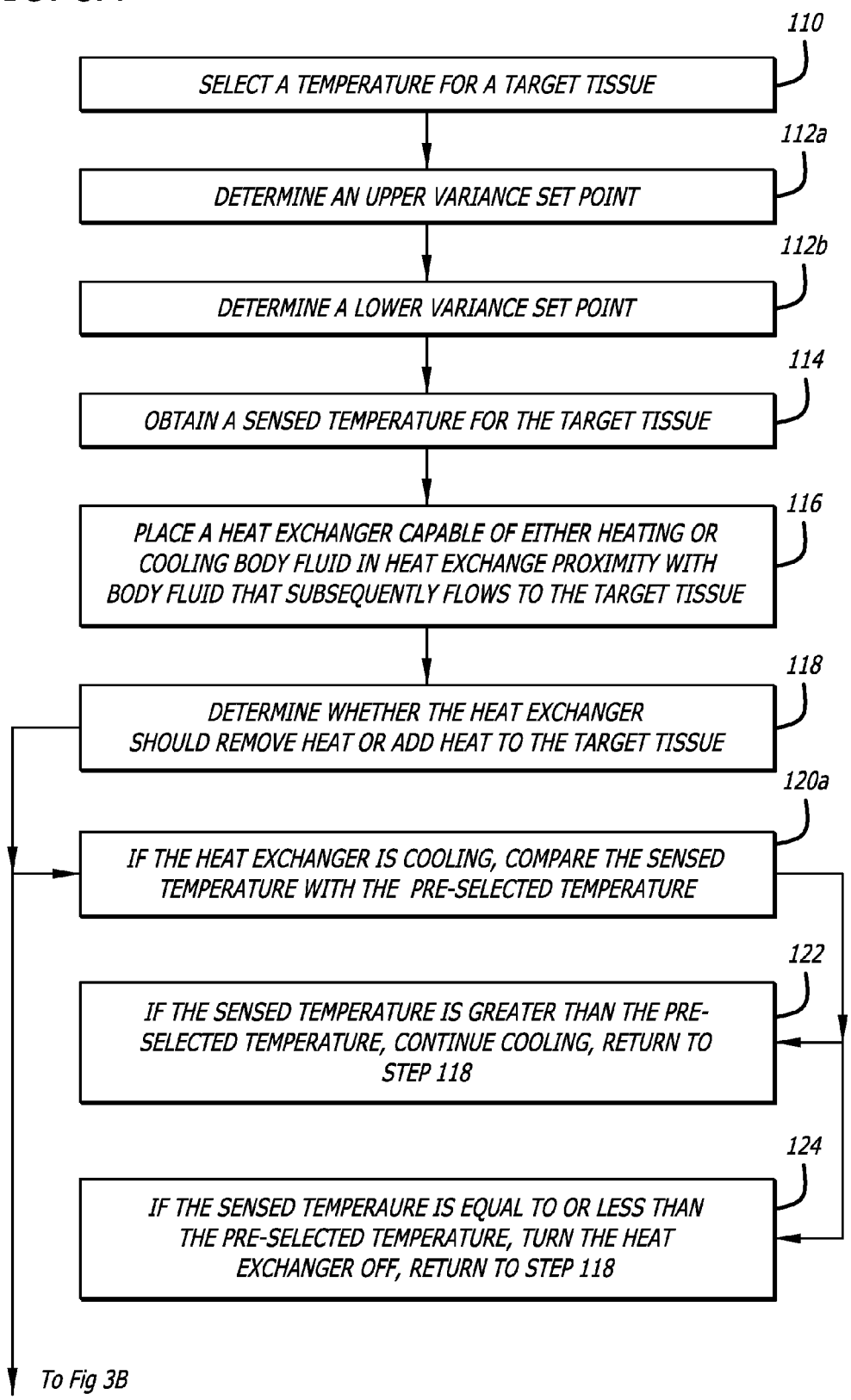
FIGS. 3A-3B together show a flowchart of a control scheme of an embodiment of the heat exchange system of the present invention.
Figure 3B:
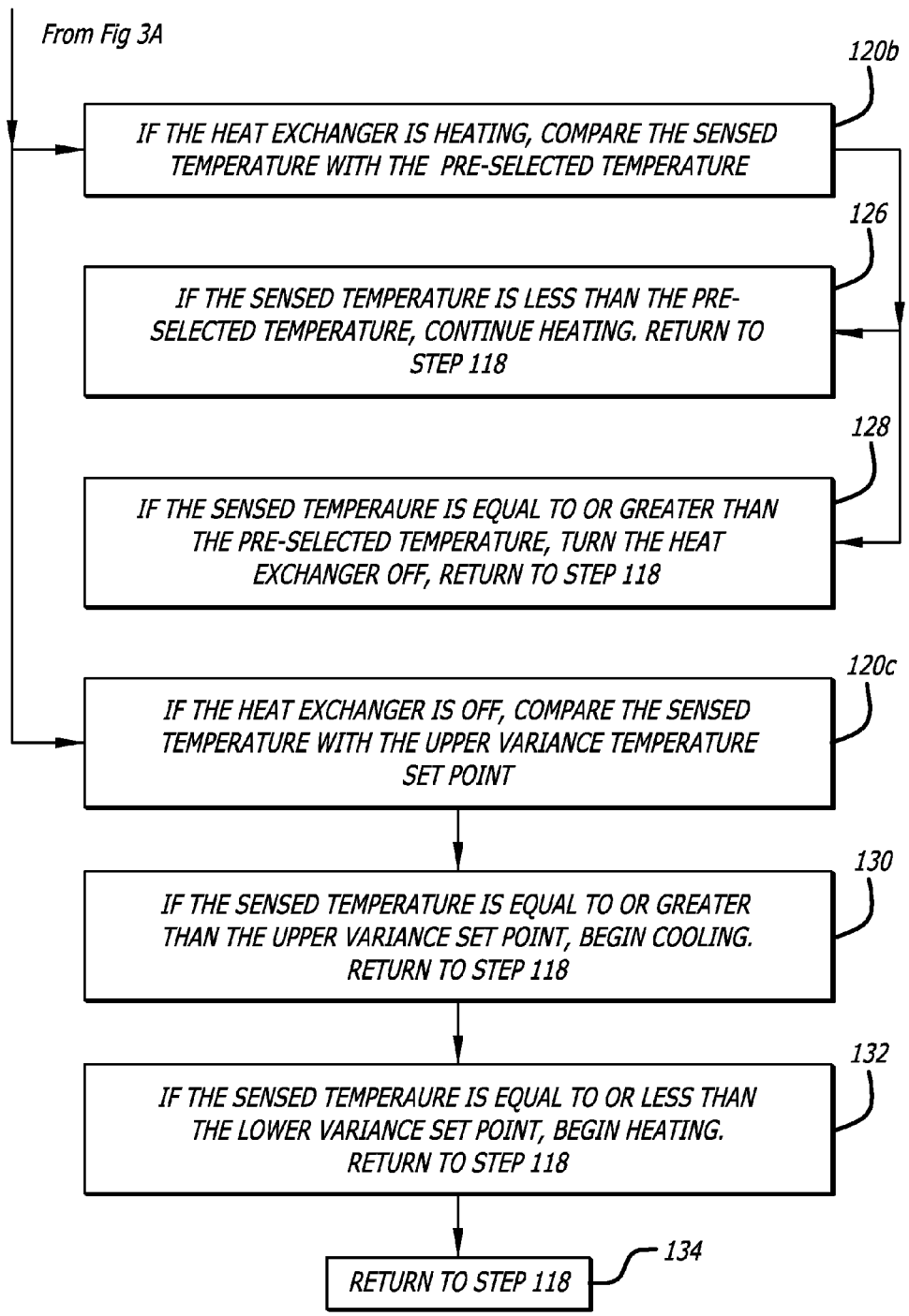

The flowchart seen in FIGS. 3A and 3B illustrates an exemplary sequence of steps that the controller processor 70 coordinates during temperature regulation of a patient. First, in step 110, a target temperature for the target tissue (which may be the entire body) is selected, generally by user input. The target temperature may be different than the body temperature, or may be the same if maintenance of normal patient temperature is the goal. Steps 112a and 112b involve determination of an upper variance set point and a lower variance set point, respectively. This is generally a pre-set buffer range above and below the target temperature that is built or programmed into the controller processor. These variance set points straddle the target temperature and create a buffer range of temperature within which the controller operates.

More specifically, the sensed temperature for the target tissue is obtained in step 114 prior to or after step 116 in which a heat exchanger capable of either heating or cooling body fluid is placed in proximity with body fluid that subsequently flows to the target tissue. Based on user input or on a comparison between the target temperature and the sensed tissue temperature a determination is made in step 118 as to whether the heat exchanger will be operating a cooling mode, a heat mode, or will remain off. That is, if the target temperature equals the tissue temperature then there will be no need to initially heat or cool the body fluid.

The determination step 118 leads to three different modes of operation of the system depending on whether the system will be COOLING, HEATING, or OFF. These modes of operation correspond to steps 120a, 120b, and 120c, which appear on both the FIGS. 3A and 3B.

If the system is in the COOLING mode, the flowchart logic leads to step 120a which compares the sensed tissue temperature with the pre-selected target temperature. If the tissue temperature is greater than the target temperature the system continues cooling as indicated in step 122, and the processor 70 returns to decision step 118. On the other hand, if the sensed tissue temperature is equal to or less than the target temperature, the heat exchanger is converted to the OFF mode as indicated in step 124 and the process 70 returns to decision step 118.

If the system is in the HEATING mode, the flowchart logic leads to step 120b which also compares the sensed tissue temperature with the pre-selected target temperature. If the tissue temperature is less than the target temperature, the system continues heating as indicated in step 126, and the processor 70 returns to decision step 118. On the other hand, if the tissue temperature is equal to or greater than the target temperature, the heat exchanger is converted to the OFF mode as indicated in step 128, and the processor 70 returns to decision step 118.

If the system is in the OFF mode the flowchart logic leads to step 120c which compares the sensed tissue temperature with the upper variance temperature set point. Then, if the sensed tissue temperature is equal to or greater than the upper variance set point, the system is converted to the COOLING mode as indicated in step 130, and the processor 70 returns to decision step 118. If the tissue temperature is less than the upper variance set point, the processor continues to step 132 in the flowchart logic, and determines if the tissue temperature is equal to or less than the lower variance set point, whereby the system is converted to the HEATING mode and processor 70 returns to decision step 118. Finally, if the tissue temperature is between the upper and lower variance set points, the system does nothing as indicated in step 134, and the processor 70 returns to decision step 118.

Figure 4:
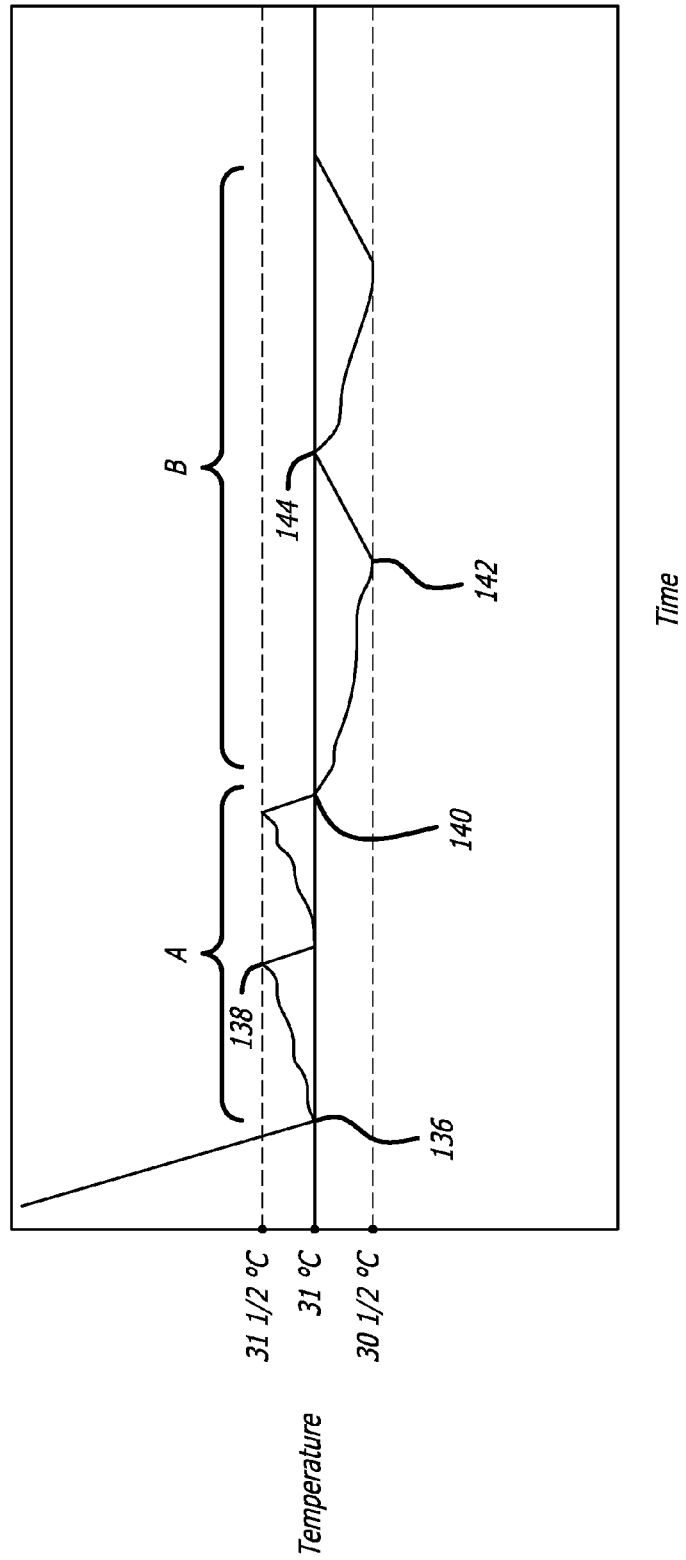
FIG. 4 is a graph of the sensed temperature of a target tissue or body fluid over time under the influence of the control scheme of FIGS. 3A-3B.

FIG. 4 is a graphical illustration plotting the fluctuating sensed tissue temperature over a period of time relative to the target temperature and variance set points. In the example, the target temperature is set at 31 degrees Celsius, with the upper and lower variance set points ½ degrees on either side. Initially, the sensed tissue temperature is greater than the target temperature, such as if the heat exchange catheter is placed in contact with blood at 37 degrees Celsius. The system is first placed in the COOLING mode so that the sensed tissue temperature is reduced until it equals the target temperature at 136, corresponding to steps 120a and 124 in FIG. 3A. In step 124, the heat exchanger is converted to the OFF mode, which results in the sensed tissue temperature climbing until it reaches the upper variance set point at 138, corresponding to step 130 in FIG. 313, at which time the system begins cooling again. This cycle is repeated in the region indicated at A.

Eventually, the patient may be unable to maintain even the target temperature as shown by the temperature profile in the region indicated at B. For example, after the sensed tissue temperature reaches the target temperature at 140, and the heat exchanger is turned OFF, the sensed target temperature may continue to drift lower until it reaches the lower variance set point at 142. The controller logic senses this in step 132 of FIG. 3B, and converts the system to the HEATING mode. Subsequently, the sensed tissue temperature climbs to the target temperature at 144, and the system is again turned OFF, corresponding to steps 120b and 128 in FIG. 3B. Alternatively, depending on the patient and the situation, it may be that after the sensed tissue temperature reaches the target temperature and the heat exchanger is turned OFF, the patient's temperature may begin to increase until it rises to the upper variance set point temperature, at which point, as described in box 130 the heat exchanger begins to COOL. As can be appreciated, the sensed tissue temperature continues to fluctuate between the upper and lower variance set points in this manner.

The control scheme as applied to the system of the present invention has the advantage of allowing the operator to essentially input a desired temperature after which time the system will automatically regulate the tissue temperature until it reaches the target temperature, and will maintain the tissue temperature at that target temperature. The buffer range created by the upper and lower variance set points prevents the controller from turning the heater/cooler on and off or activating and de-activating the pump driver in rapid succession, actions that would be potentially damaging to these electric devices.

Figure 5:
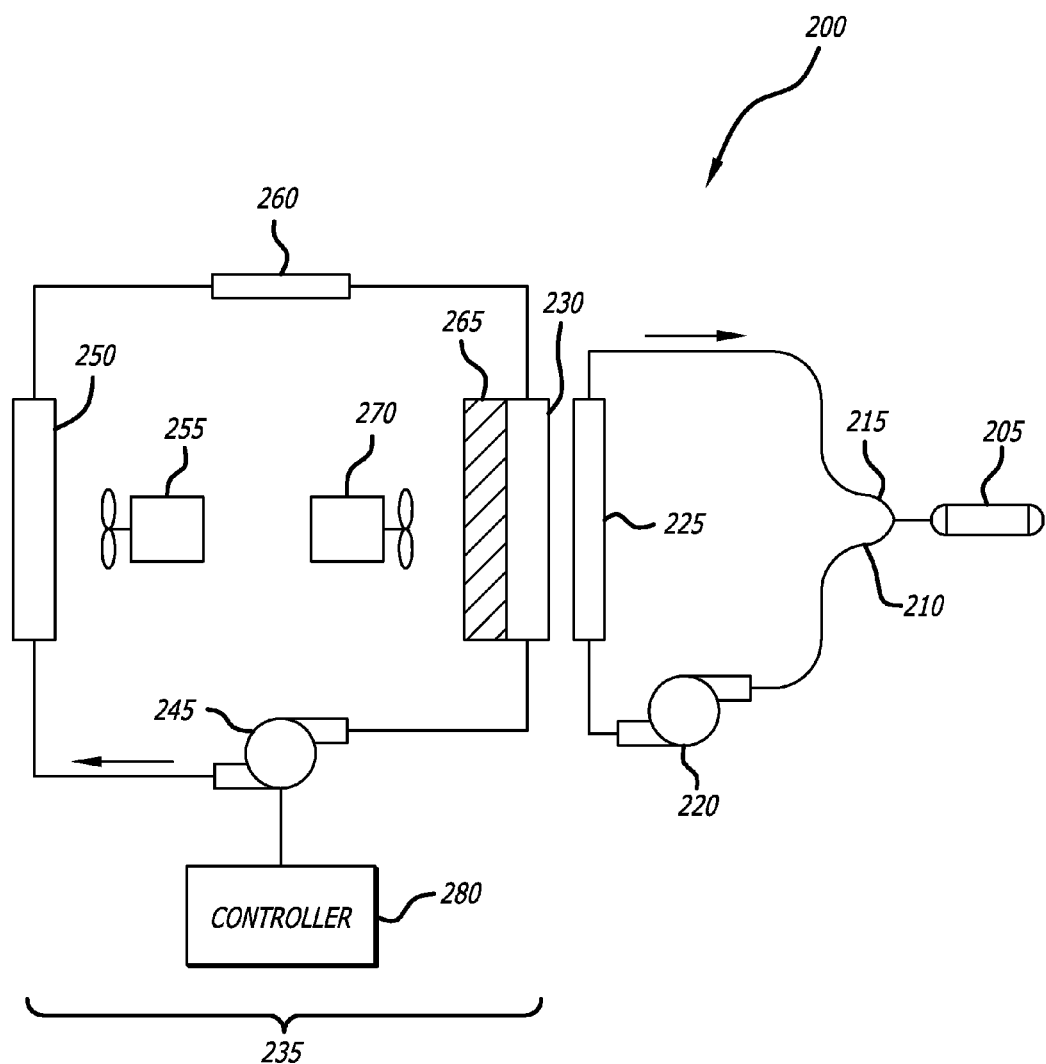
FIG. 5 is a schematic illustration of an embodiment of the present invention utilizing a two-stage heater/cooler to add or remove heat from a heat exchange fluid flowing through a heat exchange catheter.

FIG. 5 illustrates an alternative embodiment of the present invention that combines a refrigeration system capable of providing for the rapid removal of large amounts of heat from a heat exchange fluid with a system, for example, a thermo-electric system, that removes heat at a slower rate than the refrigeration system, but is more controllable as the patient's temperature approaches a desired target temperature. Additionally, the thermo-electric system provides for the addition of heat to the heat exchange fluid should the patient's temperature need to be raised.

FIG. 5 shows a heating/cooling system 200 having a heat exchange catheter 205 in fluid communication with a pump 220 and a heat exchanger 225 through fluid lines 210, 215. In this embodiment, pump 220 receives heat exchange fluid from an outlet side of catheter 205 through line 210, and pumps the heat exchange fluid through heat exchanger 225 into the inlet side of catheter 205 through line 215.

The heat exchanger 225 is typically placed in thermal contact with heat block 230. Heat block 230 is part of a primary fluid circuit 235 that is separate and not in fluid communication with the fluid circuit formed by catheter 205, pump 220, heat exchanger 225 and lines 210, 215.

Primary fluid circuit 235 utilizes a compressible fluid or gas in a typical expansion refrigeration cycle to provide for rapid removal of heat from heat block 230. As heat is removed from heat block 230, the heat block cools. When heat exchanger 225 is in thermal contact with heat block 230, heat is removed from heat exchanger 225 as the heat block cools, and thus heat is also removed the circulating heat exchange fluid circulating between heat exchanger 225 and catheter 205.

As is typical for refrigeration systems, a compressor compresses a compressible fluid or gas. The compressed fluid or gas is then cooled by routing the fluid or gas through a condenser 250. Depending on ambient conditions, and the amount of heat to be removed, condenser may optionally be cooled by a fan 255. The compressed gas or fluid then is allowed to expand through an expansion valve 260 and then into heat block 230. The expanding fluid or gas cools the heat block.

It has been observed that rapid cooling of a patient to a level thought to be protective after cardiac or stroke events requires 300-450 watts of initial cooling. Once the patient's body temperature approaches the desired target temperature, only 100-200 watts of cooling are needed to reach and maintain the target temperature. However, it is difficult to control the cooling power of primary circuit 235 because typically the speed of compressor 245 cannot be easily changed. Additionally, primary circuit 235 is only capable of removing heat from heat block 230; it cannot add heat to heat block 230 in those instances where a patient's temperature needs to be raised.

For this reason, another embodiment of the present invention includes a thermo-electric element 265 disposed in thermal communication with heat block 230. A fan 270 may be used when needed to cool thermo-electric element 265. Thermo-electric element 265 can be used to enhance the cooling power of the primary circuit 235 when the two systems are operated together. For example, primary circuit 235 may provide 100-300 watts of cooling power, and the thermo-electric element 265 may provide for an additional 150 watts of cooling, for a total of 450 watts of cooling. Alternatively, the primary circuit 235 and thermo-electric element 265 may be used in a variety of combinations to provide a wide range of cooling and heating. For example, both may be used to provide maximal cooling power so as to maximize the rate of temperature decrease of a patient body during an initial cooling phase. As the patient's body temperature approaches a target temperature, controller 280 may de-activate the compressor of the primary circuit, and control the continued cooling of the patient using only the thermo-electric element 265. Further, once the target temperature is reached, the thermo-electric element may also be controlled to heat or cool heat block 230 as necessary to maintain the patient's temperature at the target temperature.

Figure 6:
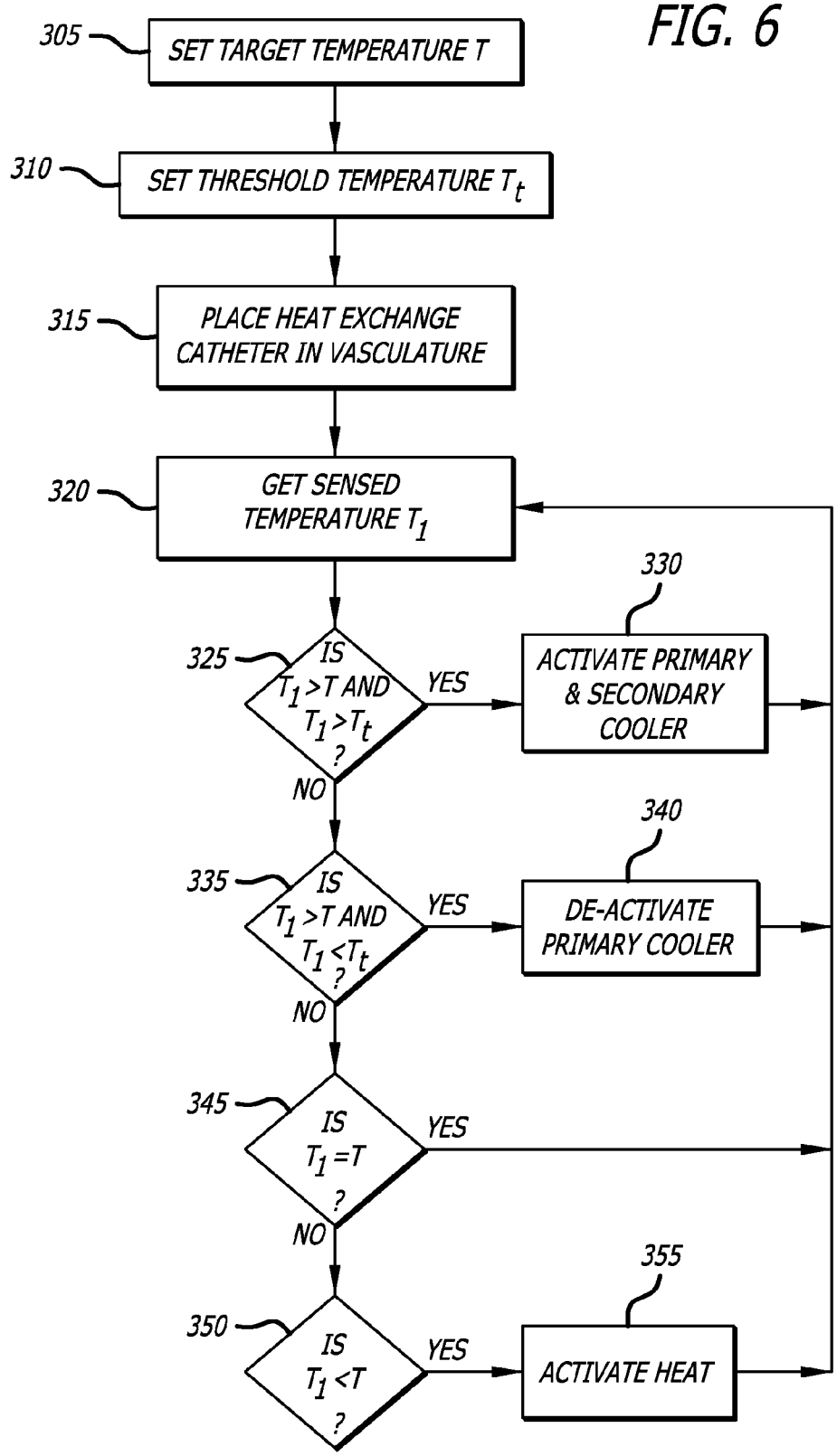
FIG. 6 is a flowchart illustrating an embodiment of a control scheme of the embodiment of FIG. 5.

FIG. 6 presents a flow chart that illustrates an exemplary method of operating the system described to manage the temperature of a patient. In box 305, the system operator enters a target temperature into the controller. As described previously, various parameters may be entered into the controller using a user interface that may include a display screen, buttons, dials or switches. Those skilled in the art will understand that one or more screens may be used, and the all of the parameters for input may be accessible using a touch screen well known to those skilled in the art. Additionally, the controller may have a communication module that allows for communication, either wired or wirelessly, with other devices, such as devices monitoring various health parameters of the patient, or with data management systems or other computers. Such data management systems may also include systems or subsystems that may be used to remotely control the various embodiments of the present invention, or which may retrieve information from the various embodiments of the present invention for inclusion in an electronic medical record associate with the patient.

The operator may set a threshold temperature in box 310. This temperature may be determined to be a temperature approaching the target temperature. At this temperature, the operator may wish to reduce the amount of cooling power being used, and thus reduce the rate of heat removal from the blood of the patient. Doing so provides for improved control of the cooling process, and prevents overshoot of the target temperature.

The heat exchange catheter is inserted in the vasculature of the patient in box 315. A temperature sensor in communication with the controller is placed on or within the patient's body to monitor the body temperature of the patient, or a portion of the patient in box 320. More than one sensor may be used to provide for more accurate monitoring of the patient's temperature. An initial body temperature is sensed and provided to the controller.

The processor of the controller, as described above, is programmed using appropriate software commands to carry out the remainder of the steps of this illustrative method, receiving input from operators and sensors and other devices in communication with the controller and controlling the primary circuit and thermo-electric element in accordance therewith.

In box 325, the processor compares the sensed temperature from box 320 to the target temperature and the threshold temperature to determine if the sensed temperature is greater than both the target temperature and the threshold temperature. If the comparison is true, that is, the sensed temperature is greater than both target and threshold temperatures, then the processor provides a command that activates the primary circuit to provide a high rate of cooling. As stated previously, in some embodiments, the processor may also activate the thermo-electric element to provide maximal cooling power. The process then returns to box 320 and repeats until temperature management of the patient is halted.

If the comparison in box 325 is false, that is, the sensed temperature is not greater than both the target and threshold temperatures, the processor performs the comparison in box 335. In this box, the processor determines whether the sensed temperature is greater than the target temperature, but less than the threshold temperature. If the comparison is true, then the processor generates a command that de-activates the primary circuit and either maintains or turns on the thermo-electric element to continue cooling the patient in box 340. The process then returns to box 320 and repeats until temperature management of the patient is halted.

If the comparison in box 335 is false, then the processor attempts to determine if the sensed temperature is equal to the target temperature in box 345. If the comparison is true, then the processor may reduce the power to the thermo-electric element to reduce the rate of cooling provided to just balance the amount of heat being naturally supplied by the patient's life processes. Alternatively, the thermo-electric element may be turned off completely. The process then returns to box 320 and repeats until temperature management of the patient is halted.

If the comparison in box 345 is false, then the process determines if the sensed temperature is less than target temperature in box 350. If the comparison is true, then the processor generates a command to the thermo-electric element to cease cooling and to begin to provide heat to warm the blood of the patient in box 355. The process then returns to box 320 and repeats until temperature management of the patient is halted.

It will be understood that the controller will be programmed to prevent unnecessary cycling of the compressor as the sensed temperature reaches the target temperature. The algorithms used to determine when to activate or de-activate the compressor will include lags that take into account hysteresis of the system so that once target temperature is reached, the temperature will have to rise a selected amount before the controller will command the compressor to turn on. Similarly, once the compressor is turned on, a selected amount of overshoot of the target will be allowed to protect the compressor form short cycling.

Exemplary heat exchange control unit

FIGS. 7A-5C are various views of an exemplary heat exchange control unit 400 of the present invention that is particularly suited for rapid temperature regulation of a patient. As seen in the Figures, the control unit 400 comprises a vertically-oriented outer housing having a lower portion 405 and upper portion 410 separated at a generally horizontal dividing line 415 located close to the top of the unit. The control unit 400 is mounted on wheels 420 for ease of portability, with the wheels preferably being of the swivel type having foot-actuated locks. For ease of servicing, the upper and lower portions may be joined together with hinges 425 (not shown) at the back so that the top portion may be lifted up and rotated back to expose the interior of the unit. In an exemplary embodiment, the control unit 400 has a height that enables an operator to easily access an upper control panel 430 without the need for significant bending. For example, the control unit 400 may have a total height of between approximately 2-3 feet, and preferably about 32 inches. The substantially horizontal cross-section of a majority of the control unit 400 may have widths of between one and two feet, although the lower portion 405 preferably widens at its lower end with the wheels 420 mounted on the lower corners to provide greater stability.

Figure 7B:
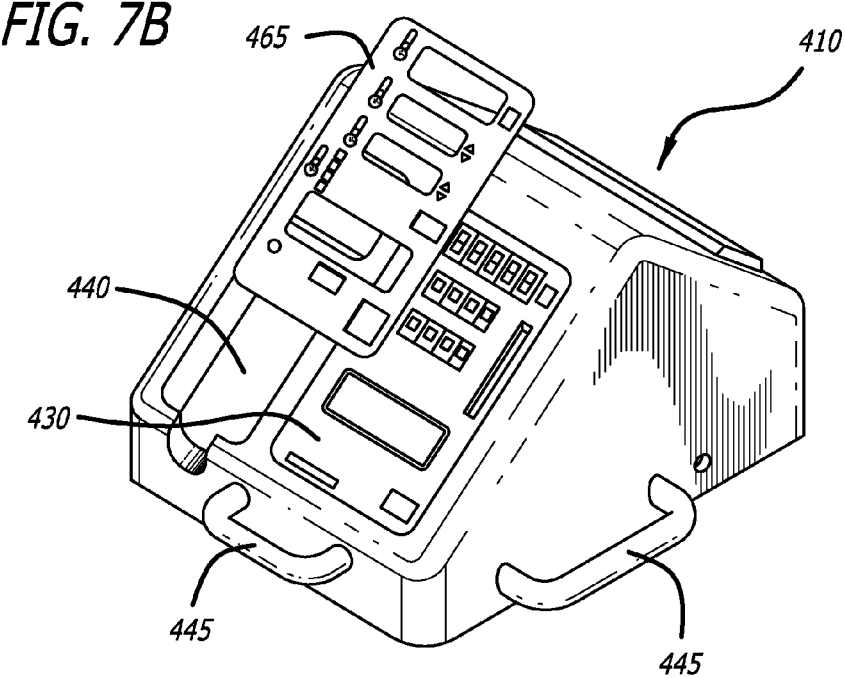
FIG. 7B is a perspective view of an upper portion of the control unit of FIG. 7A.
Figure 7C:
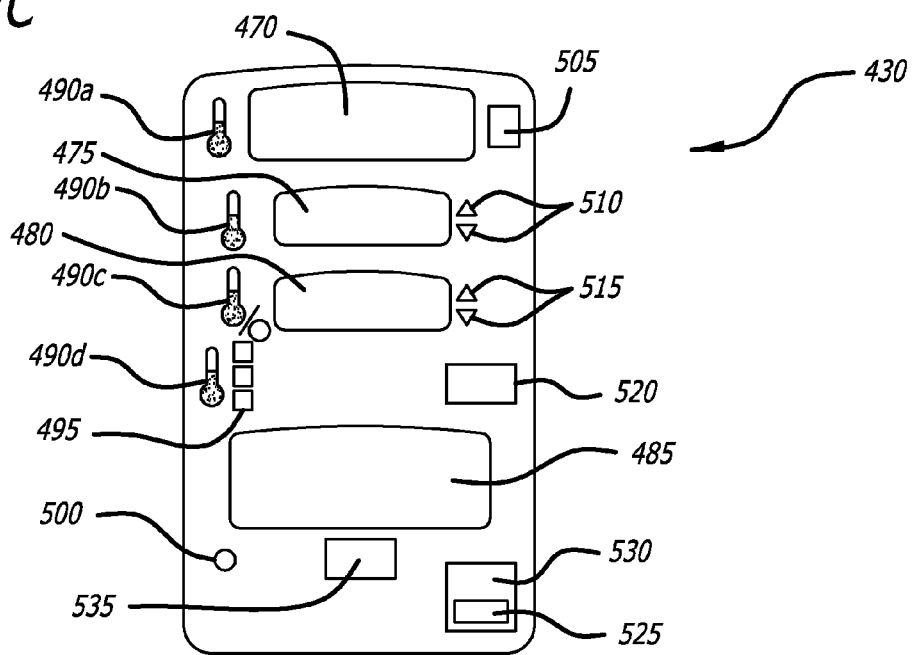
FIG. 7C is a plan view of an exemplary control panel for the control unit of FIG. 7A.

FIG. 7A illustrates the assembled control unit 400, while FIGS. 7B-7c show various exploded views and subassemblies of the control unit. FIG. 7A illustrates the front and right sides of the unit 400 wherein the control panel 430 is visible on an angled upper panel 435 of the upper portion 410 front side. The angled upper panel 435 also defines a fluid container receiving cavity 440 adjacent the control panel 430. Further, a plurality of handles 445 may be provided to help maneuver the control unit 400.

A heat exchange cassette-receiving opening 450 is also provided on a front panel 455 of the control unit 400, just below the horizontal dividing line 415. As will be explained below, the opening 450 is sized and shaped to receive a heat exchange cassette of the present invention, analogous to the heat exchange cassette-receiving opening 102 shown in FIG. 2. Likewise, the control unit 400 provides all of the features that were described above for the control unit 50 of FIG. 2, including a heater/cooler, a pump driver, a controller processor/microprocessor, and a manual input unit, namely the control panel 430.

Because of the relatively high capacity for heating and cooling, the lower portion 405 of the control unit housing includes a plurality of vents 460 to facilitate convective heat exchange between the interior of the housing and the surrounding environment. The control unit housing may be manufactured of a number of suitably strong and corrosion-resistant materials, including stainless-steel, aluminum, or molded plastic. Desirably, the components of the control unit 400 are adapted to run on conventional power from a catheterization lab power outlet, for example.

Exemplary control panel

FIGS. 7B and 7C illustrate in greater detail the upper portion 410 of the control unit 400, and in particular the control panel 430. FIG. 7B shows a facade 465 exploded from the control panel 430, with the facade shown in FIG. 7C having indicia printed thereon corresponding to various displays and buttons. (The reader will notice that the control panel 430 in FIG. 7C is an alternative embodiment from one shown in other drawings, and includes several added features and with several buttons and/or displays being slightly relocated).

The exemplary control panel 430 of FIG. 7C provides a number of visual displays, including, from top to bottom along the centerline, a patient temperature display 470, a target temperature display 475, a cooling/warming rate display 480, and a system feedback/status display 485. Other desirable information may be displayed, either with an additional display, or alternating with information displayed on one of the screens shown here, or by user initiated request from one of the screens shown here. For example, by way of illustration but not limitation, if the ramp rate for heating or cooling the patient is set by the user, or is calculated by a control microprocessor, or the projected time to target temperature is calculated, those values may be shown. The larger displays for alphanumeric characters are preferably liquid crystal displays (LCD), while several light emitting diode (LED) status indicators are also provided. Touch screens may also be used. Several graphic icons are positioned adjacent the left of the upper three LCD displays 470, 475, and 480, to indicate their respective display functions. Specifically, a patient temperature icon 490a, a target temperature LED 490b, and a cooling/warming rate LED 490c are provided. Just below the cooling/warming rate LED 490c, an operational mode LED 490d and associated vertical series of three mode indicators 495 are provided. Only one of the indicators 495 lights up at any one time, depending on whether the system is in the COOLING, WARMING, or MAINTAINING mode. In lieu of the mode indicators 495, the display 485 may carry the message COOLING PATIENT, WARMING PATIENT, or MAINTAINING so that the operator can easily identify the mode of functioning of the controller. There also may be only one patient temperature icon 490 which has a line of lights that streams upward if the unit is warming, downward if the unit is cooling, and blinks stationary if the unit is maintaining. Finally, a power on/off indicator LED is provided in the lower left corner of the control panel 430.

The control panel 430 also exhibits a number of input buttons including, in descending order on the right side of the control panel, a Celsius/Fahrenheit display toggle 505, a pair of target temperature adjustment buttons 510, a pair of cooling/warming rate adjustment buttons 515, a multi-function/enter button 520, and a mute audible alarm button 525. The mute audible alarm button 525 is nested within an LED alarm indicator 530. Finally, in the lower central portion of the control panel 430, a stop system operation button 535 permits instant shutdown of the system.

The buttons and displays described above are illustrative of one embodiment of the present invention, and are not intended to be limiting. Other display types and input devices or ports may also be provided depending on the needs of the designer. For example, touch screen technology may be used to combine the screens and input devices into an operator friendly interface. Additionally, the processor of the controller may be programmed such that the display and input means present the operator with a fool-proof means for entering operating parameters and/or patient information into the system, and to display not only information related to the set-up and function of the system, but may also be used to present information related to one or more health parameters of the patient, or other information useful to the operator.

Alternative console embodiment

Figure 8:
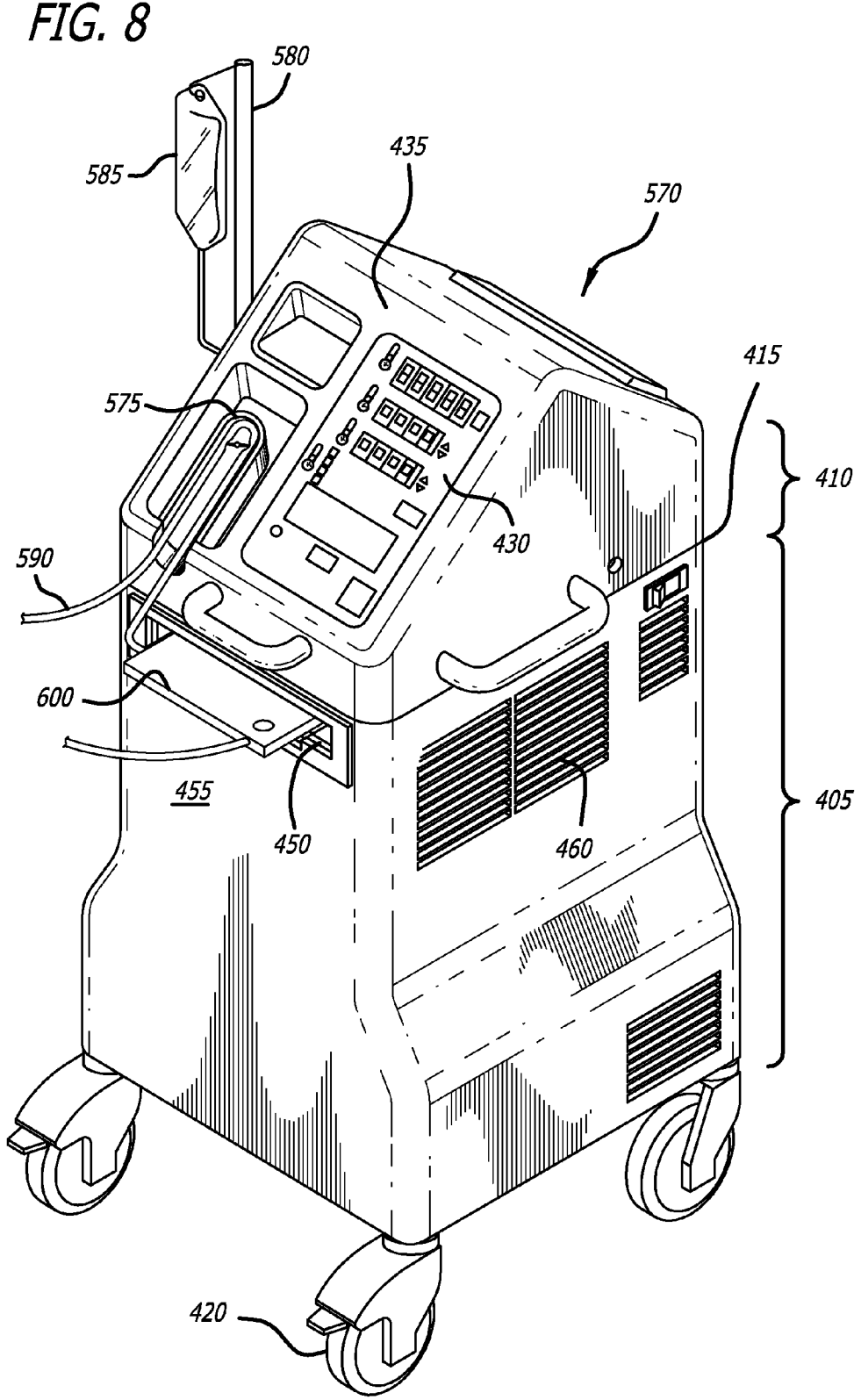
FIG. 8 is a perspective view of another embodiment of a re-usable control unit of the present invention illustrating an exemplary placement of a peristaltic pump and fluid supply.

FIG. 8 shows an alternative embodiment of the control unit of FIG. 7A. Like reference numerals in FIG. 8 refer to like components of the control unit of FIG. 7A. In this embodiment, control unit 570 is shown having an externally mounted peristaltic pump 575 that is used to pump heat exchange fluid through a fluid circuit comprising a heat exchanger, tubing and a heat exchange catheter. An IV bag arm 580 holding an IV bag 585 for supplying heat exchange fluid to prime the fluid circuit is also shown. Fluid line 590 communicates heat exchange fluid from the heat exchange catheter to peristaltic pump 575 which pumps the heat exchange fluid through heat exchange cassette 600, shown inserted into slot 450 of the control unit, and then through fluid line 595 to the heat exchange catheter. This embodiment is advantageous in that it provides for easy mounting of the tubing line in the peristaltic pump, along with insertion of the heat exchange cassette 600 in to the control unit, allowing for rapid set-up or change-over of the unit for use with a patient.

Figure 9A:
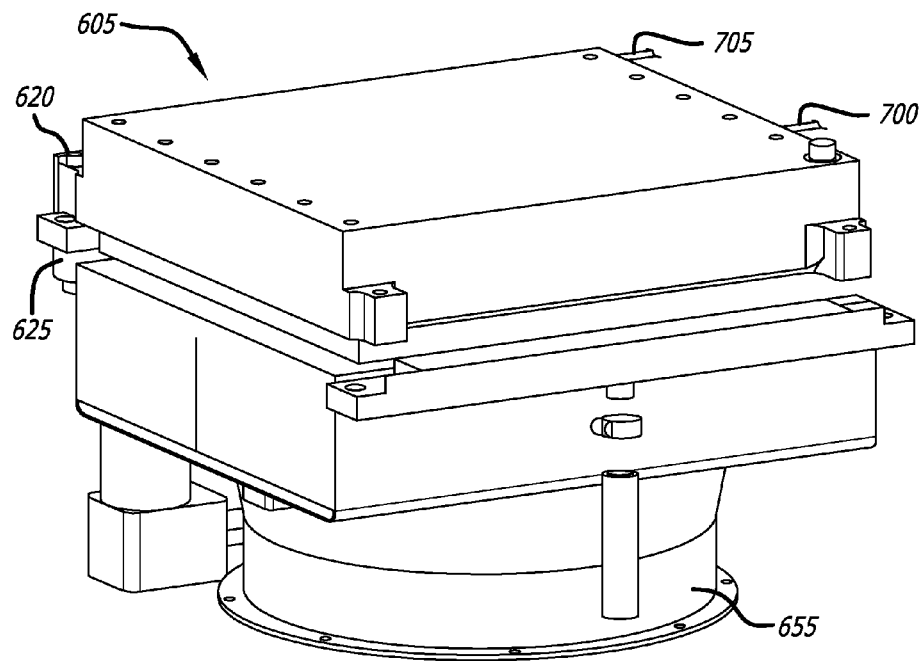
FIG. 9A is a perspective view of the heat exchange cassette-receiving subassembly.
Figure 9C:
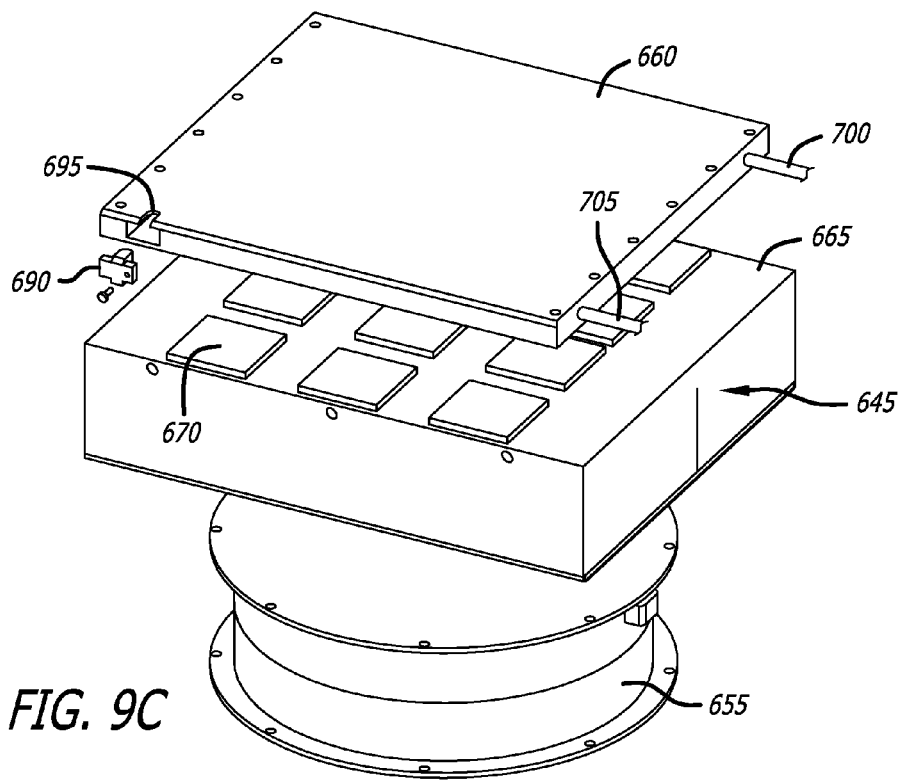
FIG. 9C is an exploded view of a heater/cooler unit of the heat exchange cassette-receiving subassembly of FIG. 9A.
Figure 9B:
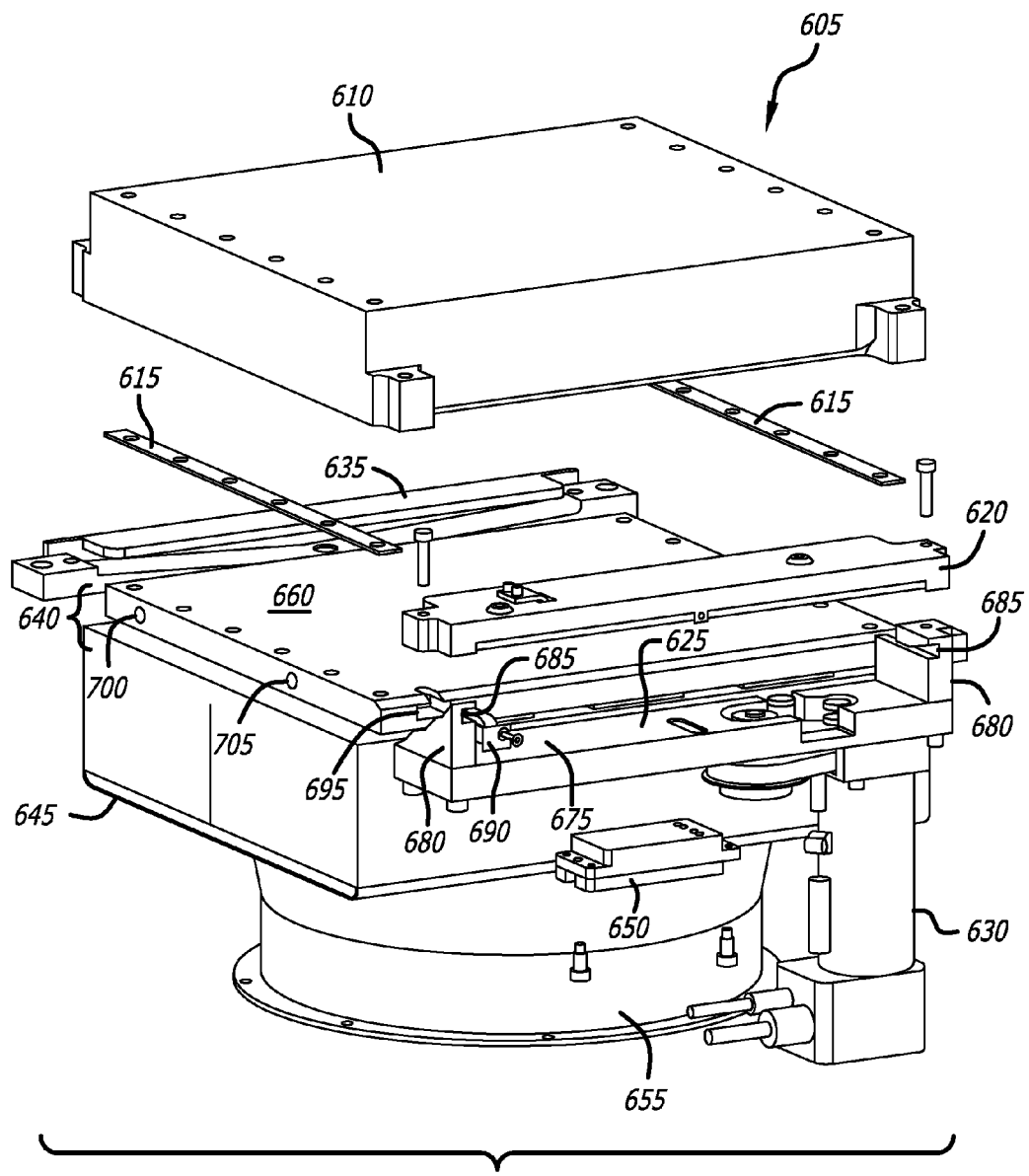
FIG. 9B is an exploded view of the heat exchange cassette-receiving subassembly of FIG. 9A.

FIGS. 9A-9C further illustrate the various components of one embodiment of a heat exchange cassette-receiving subassembly 605 in several views and with several portions removed or exploded. With reference first to FIG. 9B, the subassembly 605 comprises, from top to bottom, an upper pressure plate 610, a pair of elongated side spacers 615, an upper guide assembly 620, a lower guide assembly 625, a pump drive mechanism 630 attached to and depending downward from the lower guide assembly, a rear water channel assembly 635, a heater/cooler subsystem 640, and an air cooler 645 disposed directly below the heater/cooler subsystem. In addition, a fluid level measurement sensor module 650 is shown exploded in FIG. 6B, and is adapted to be mounted to the underside of the lower guide assembly 625.

The air cooler 645 comprises a hollow box-like structure having solid front and rear walls, a circular opening (not shown) in the bottom wall to communicate with the interior of the tubular skirt 655. In addition, the air cooler 645 is exposed to the underside of the heater/cooler subsystem 640. This is accomplished by fastening a portion of the heater/cooler subsystem 640 over the open-topped box of the air cooler 645, as will be described in greater detail below with respect to FIG. 6C. In this manner, air blown through the tubular skirt 655 (either upward or downward) flows past the underside of the heater/cooler subsystem 640. The air cooler 645 therefore acts as a highly efficient convective heat sink for the heater/cooler subsystem 640. Of course, other types of heat sinks and other patterns of convective air cooling may be used, and the present invention should not be considered limited to the air blower 645 shown.

FIG. 9C shows the heater/cooler subsystem 640 exploded with an upper plate 660 separated from a lower plate 665 and between which a plurality of thermoelectric (TE) modules 670 are sandwiched in thermal contact with both. As mentioned previously, the lower plate 665 fastens over the open top of the box-shaped air cooler 645. The TE modules 670 are preferably discrete modules distributed over the surface of the lower plate 665. In the exemplary embodiment illustrated, there are twelve square TE modules 670 distributed in rows and columns across substantially the entire area of the lower plate 665.

The TE modules 670 preferably function on the well-known Peltier principal, wherein the same TE modules may either heat or cool depending on the direction of DC current through the units. Therefore, merely by changing the polarity of the current flowing through the TE module the heater/cooler subsystem can be instantly changed from a heater to a cooler or vice versa. The amount of heat or cold generated can also be adjusted by controlling the amount of current flowing through the TE modules. Thus a very high level of control may be exercised by control of only one variable, the DC current supplied to the TE modules.

The upper plate 660 provides a conductive heat transfer interface between TE modules 670 and the heat exchange cassette inserted within the cavity 675 (FIG. 9B), and tends to distribute the discrete temperature differentials provided by the TE modules 270 over its surface. This helps to prevent localized heating or cooling of the heat exchange cassette, which may provoke an erroneous temperature measurement. Further, the upper plate 660 is manufactured of a suitably rigid metal having good thermal conductivity, such as anodized aluminum or other suitable material. The rigidity of both the upper plate 660 and the upper pressure plate 610 are sufficient to resists bending from fluid pressurization of the heat exchange cassette positioned in the internal cavity 675.

With reference again to FIGS. 9A and 9B, connection of the various components of the subassembly 605 creates the aforementioned internal cavity 675 into which a heat exchange cassette of the present invention can be inserted. A heat exchange cassette, similar in some embodiments to that shown in FIG. 2, is provided comprising a relatively thick bulkhead portion and a relatively thin external heat exchanger, with the external heat exchanger sized to fit between the upper pressure plate 610 and the upper plate 660 of the heater/cooler assembly 640. In this regard, the lower guide assembly 625 includes a pair of upstanding side walls 680*a*, 680*b* each having guide slot 685*a*, 685*b* facing inward toward the other. The guide slots 685*a*, 685*b* are sized to receive the side edges of the desirably plate-like external heat exchanger and reliably directed it into the narrow gap defined between the upper pressure plate 610 and the upper plate 660. Although not shown, a micro-switch may be provided in a slot in of one of the upstanding side walls 680 to indicate when the heat exchange cassette has been fully inserted into the internal cavity 675, and is engaged therein for proper operation of the system. Also not shown but well known in the relevant art, registration means such as pressure pins or balls and mating detents may be provided in the control unit and cassette respectively to aid in the correct relative positioning between the cassette and the control unit.

FIGS. 9B and 9C illustrate a thermistor 680 positioned in a similarly-shaped receptacle 695 in one edge of the upper plate 660 of the heater/cooler subsystem 640. The thermistor 690 may be of a standard type well known in the art and generally available, and is secured in the receptacle 695 with a fastener, such as the screw shown exploded in the figures. The thermistor 690 senses the temperature of the upper plate 660 and is connected (not shown) to transmit the information to the control processor of the control unit. The temperature of the upper plate 660 provides a surrogate temperature of the heat exchange fluid within the heat exchange cassette positioned in the internal cavity 675. That is, the temperature of the working fluid at the heat exchanger is measured indirectly by sensing the temperature of the upper plate 660. This indirect method has been shown to work adequately, but of course a more direct measurement of the fluid temperature is within the scope of the invention.

FIGS. 9A-9C also show another embodiment of the present invention wherein upper plate 660 may be modified to be cooled by a refrigerant, as described above. In this embodiment, upper plate 660 may be manufactured to have a one or more internal channels connecting an inlet port 700 and an outlet port 705. A refrigerant, such as a compressible or gas or fluid, is allowed to expand within the internal channels of upper plate 660 to cool upper plate 660. This embodiment, as discussed previously, allows for rapid cooling of upper plate 660, and also provides for a significant amount of heat to be removed from the heat exchange fluid circulating with the fluid circuit comprising the heat exchange cassette and heat exchange catheter. It will also be understood that the relative dimensions of the various components shown in FIGS. 9A-9C are only exemplary. For example, the thickness of upper plate 660 may be increased or decreased relative to the other components of sub-system 640 without departing from the scope of the intended invention.

Electronic Control Circuit of the Present Invention

As an alternative to the control system described in conjunction with FIGS. 3A-3B and the graph of FIG. 4, the controller may employ other control schemes, for example, but not limited to, a cascading PID control scheme. In such a scheme, a control system is provided that may be divided into two sections: (a) a Bulk PID control section which takes input from the user (in the embodiment shown, RAMP RATE and TARGET TEMPERATURE) and input from the sensors on the patient representing patient temperature, and calculates an intermediate set point temperature (SP1) and an output signal to the Working Fluid PID control; and (b) the Working Fluid PID control, that receives input from the Bulk PID control section and from a sensor representing the temperature of the working fluid, and generates a signal that controls the amount of heat being removed from the heat exchange fluid circuit by activating/de-activating the primary refrigeration circuit or altering the temperature of the TE cooler by varying the power input to the TE cooler. The working fluid circulates in heat transfer proximity to the heat block (FIG. 5), so the Working Fluid PID essentially controls the temperature of the working fluid. In this way, the control scheme is able to automatically achieve a specified target temperature at a specified RAMP RATE based on input from sensors placed on the patient and the logic built into the controller. Additionally, this scheme allows the unit to automatically alter the patient temperature very gradually the last few tenths of a degree to achieve the target temperature very gently and avoid overshoot. Once the target temperature is achieved, the system continues to operate automatically to add or remove heat at precisely the rate necessary to maintain the patient at the target temperature.

Suitable heat exchange cassettes for use in the invention are described in U.S. Pat. Nos. 6,620,188, 6,620,189 and 7,806,015, the entirety of which are incorporated in full herein by reference.

Methods for Priming the Heat Exchange Catheter System

Figure 10A:
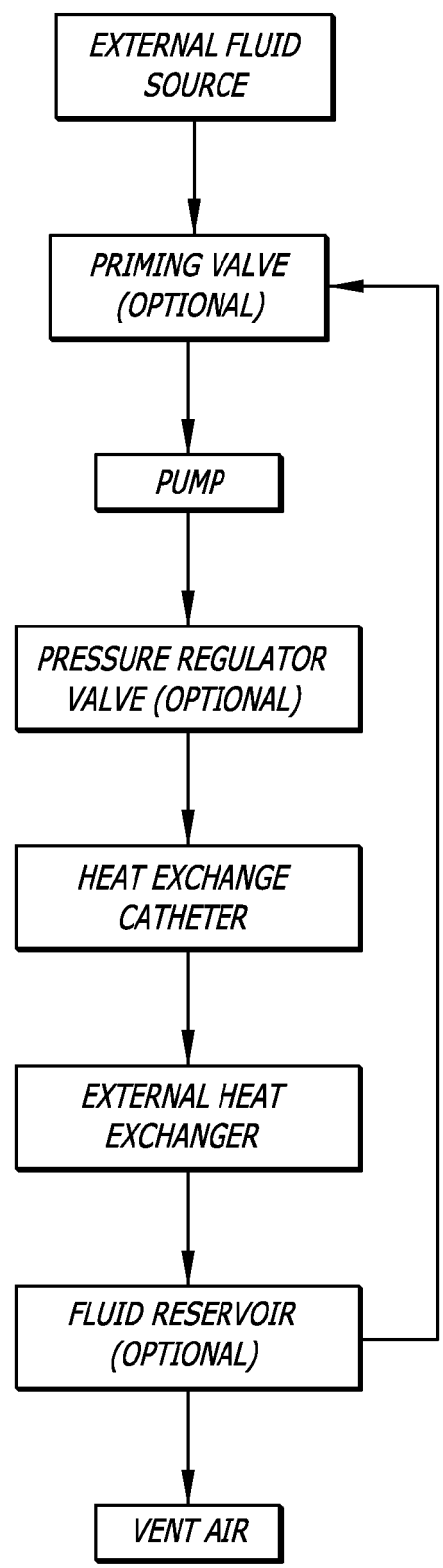
FIGS. 10A-10C are schematic illustrations of the fluid flow using different embodiments of the disposable heat exchange cassette of present invention.
Figure 10B:
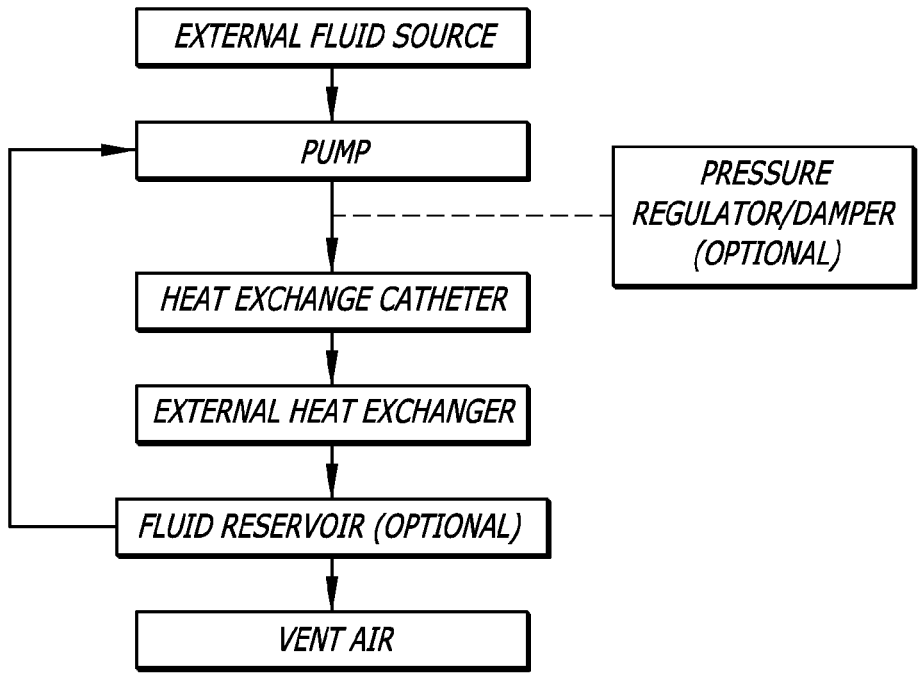
Figure 10C:
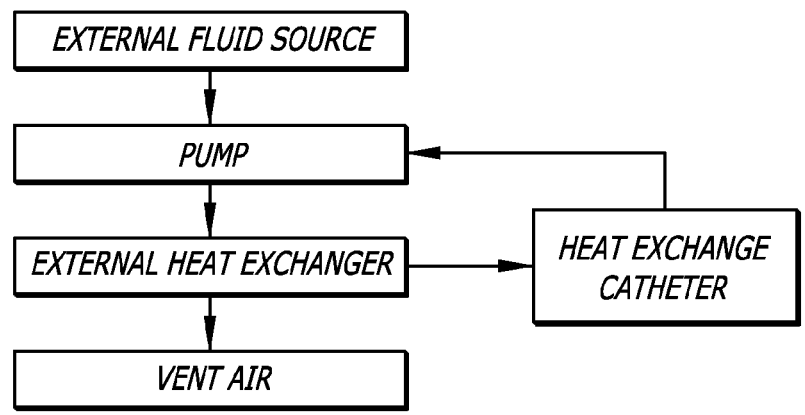

Referring to FIGS. 10A-10C, several methods of supplying heat exchange fluid to an intravascular heat exchange catheter are illustrated by fluid flow pathways, each pathway illustrating a different embodiment of the heat exchange cassette of the invention. In these embodiments, fluid flows from the pump to the heat exchange catheter, returns from the catheter and passes through the external heat exchanger, and then enters a fluid reservoir. From the reservoir, the fluid moves to the pump, and the cycle repeats for the desired duration. An optional pressure regulator can be position in the fluid path moving from the pump to the catheter. Fluid is provided from an external fluid source, which in the embodiment of FIG. 10A enters a priming valve (not shown) disposed in conduit 62 (FIG. 1), and in the embodiments of the FIGS. 10B and 10C directly enters the pump. Various method for priming the heat exchange fluid circuit are described in U.S. Pat. No. 6,620,189, the entirety of which is incorporated in its entirety herein.

It should be noted that priming of the system occurs prior to the insertion of the heat exchange catheter into the patient, with the heat exchange balloon outside the body. Indeed, the heat exchange balloon is desirably restrained within a protective tubular sheath, or is otherwise radially constrained, to prevent inflation thereof during priming. Once priming is complete, the pump motor is halted, the protective sheath is removed, and the catheter is inserted to the desired location within the patient. The sheath thus ensures a radially compact profile of the catheter during priming of the system and subsequent intravascular insertion, which prevents injury and facilitates the insertion so as to speed up the procedure.

Alternative embodiments of the cooling circuits

Figure 11:
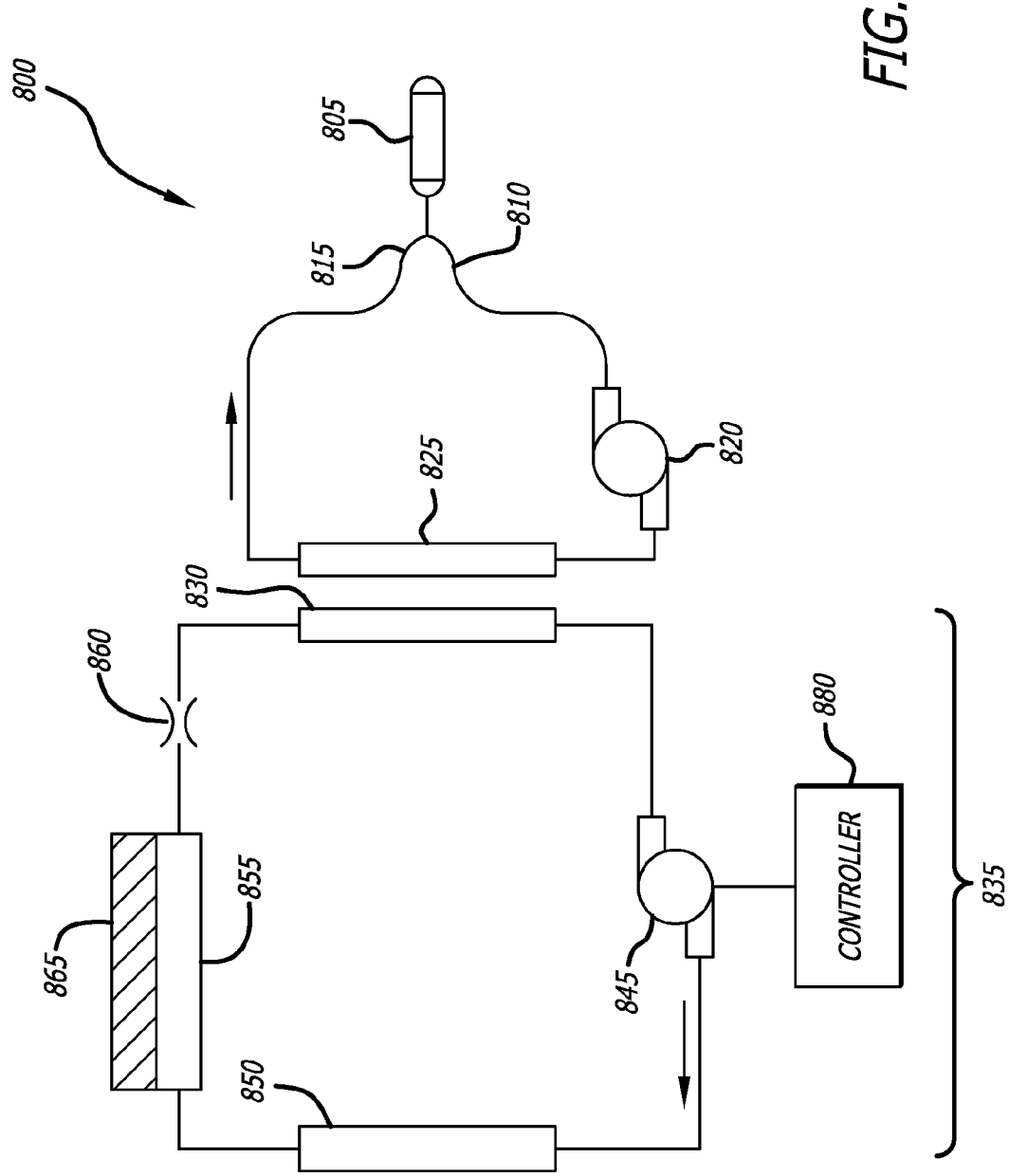
FIG. 11 is a schematic illustration of an alternative embodiment of the heater/cooler circuits of FIG. 5.

FIG. 11 illustrates an alternative embodiment 800 of the system shown in FIG. 5. As in FIG. 5, a heat exchange catheter 805 is part of a fluid circuit formed by output line 810, pump 820, external heat exchanger 825 and input line

815. A heat exchange fluid, typically saline, is circulated through this circuit to add or remove heat from a patient's vascular system, into which the heat exchange catheter is inserted.

In this embodiment, a primary heating/cooling circuit 835 comprises a heat exchange block 830 (which may be alternatively referred to as a cold block, or hot block, depending on the mode of operation of the system), a compressor 845 that compresses a compressible fluid, such as a refrigerant or other gas, and pumps the compressible fluid or refrigerant through a condenser 850. Depending on operation environmental factors, such as the ambient temperature, a fan (not shown) may be used to assist cooling of the condenser. The compressible fluid or refrigerant then flows into a second heat exchange block 855. A thermo-electric heater/cooler 865 is mounted in thermal communication with the second heat exchange block 855. Once the compressible fluid or refrigerant exits from the second heat exchange block 855 it flows through an expansion valve 860 where it is allowed to expand into heat exchange block 830, cooling block 830. Alternatively, heater/cooler 865 may be mounted in thermal communication with heat exchange block 830; in this case, the compressor may be shut down entirely if the additional cooling power provided by the compressor is not needed.

In this embodiment, compressor 845 may run continuously providing a constant amount of heat removal. Unlike the previously described embodiment, however, controller 880 may control thermo-electric heater/cooler 865 to add or remove heat to the compressible fluid flowing through second heat exchange block 855 to control the temperature, and thus the density, of the compressible fluid. In this way the amount of heat addition or removal provided by the refrigerant to block 830 may be controlled so as to vary the amount of heat added to or removed from the patient's vasculature by the heat exchange catheter. Alternatively, the compressor may be a variable speed compressor; in this case the compressor speed may be reduced to provide reduced cooling power.

Figure 12:
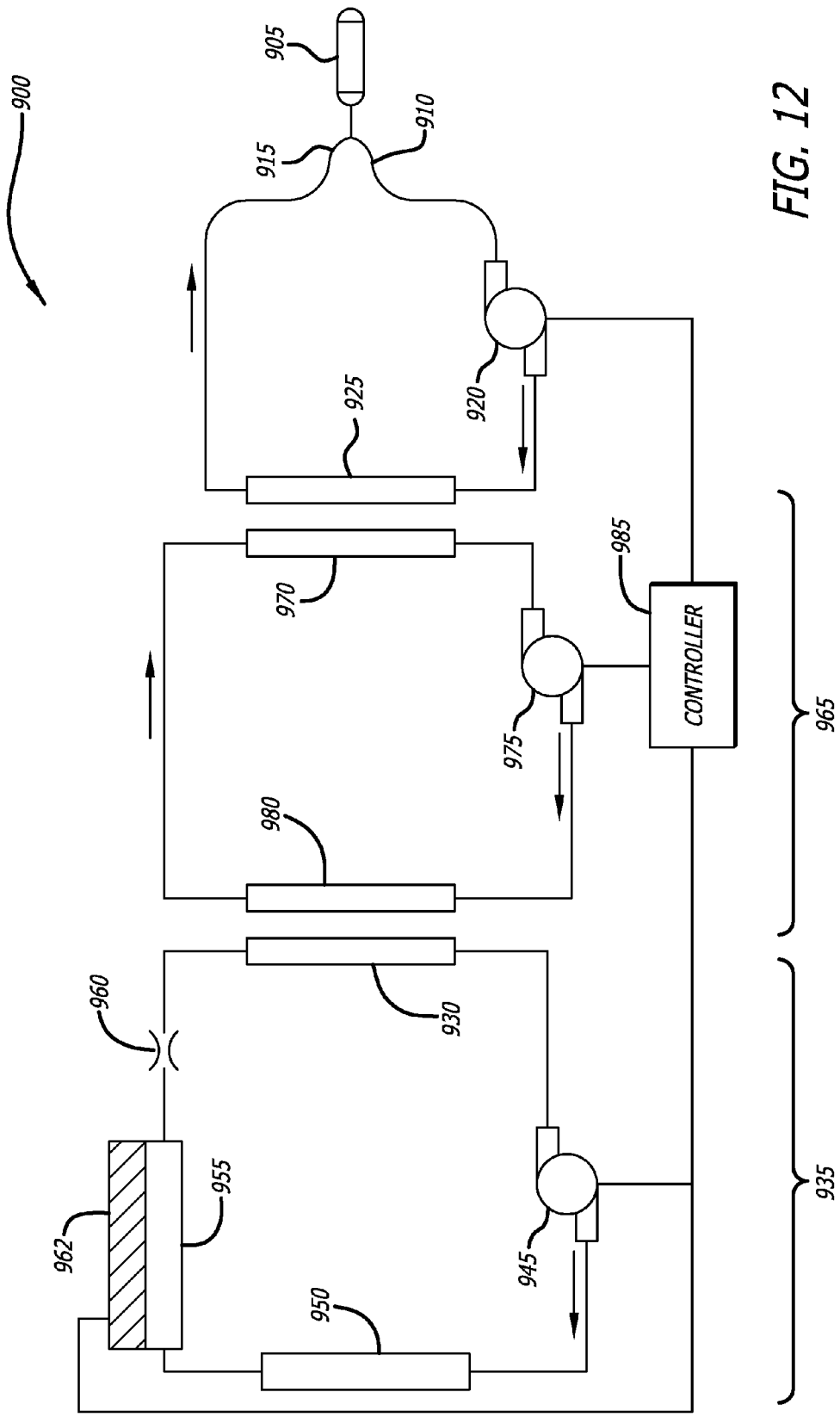
FIG. 12 is a schematic illustration of an embodiment of the present invention showing the use of a primary refrigeration loop and a secondary glycol loop to add or remove heat from a fluid circuit including a heat exchange catheter.

FIG. 12 is a schematic representation of another embodiment of the present invention which utilizes a three-stage system for removing or adding heat to the blood flowing through a patient's vasculature. Similar to previous embodiments described above, this embodiment includes a fluid circuit, typically using saline or other bio-compatible fluid as a heat exchange medium, comprising a heat exchange catheter 905 connected to an input line 915 and an output line 910. A pump 920 pumps the fluid in the fluid circuit, as shown by the arrows, from the output line 910 through a heat exchanger 925, then through the input line 915 and into the heat exchange catheter 905.

The embodiment of FIG. 12 includes a primary cooling/heating stage 935 similar to that of the embodiment of FIG. 11. In this embodiment, a compressor 945 compresses a compressible fluid or refrigerant and pumps it through condenser 950. After passing through the condenser, the refrigerant or compressible fluid passes through block 955, where it may be cooled additionally by thermo-electric heater/cooler 962, or alternatively, warmed by thermo-electric heater/cooler 962 when the thermo-electric heater cooler is operated in a warming mode. The compressible fluid or refrigerant then flows through block 930, which is constructed as a heat exchanger.

Block 930 is in thermal communication with block 980 in a manner that provides for the removal or addition of heat to a heat exchange fluid flowing through a secondary cooling/heating stage 965. Stage 965 includes a pump 975 that circulates a heat exchange fluid or other medium through the circuit of the stage comprising block 980, block 970 and pump 975. Block 970, similar to block 980, is configured as a heat exchanger to exchange thermal energy between the secondary stage and the fluid circuit comprising block 925, input line 915, heat exchange catheter 905, output line 920 and pump 920.

The heat exchange medium used in secondary stage 965 may be any fluid, such as a glycol or other heat exchange fluid. Use of glycol fluid, for example, would allow block 970 to be configured as a glycol bath in one embodiment, into which block 925 is inserted. Pump 975 would circulate the glycol from the bath into block 980 where the glycol would be heated or cooled depending on commands from controller 985 in response to the temperature of the patient.

Figure 13:
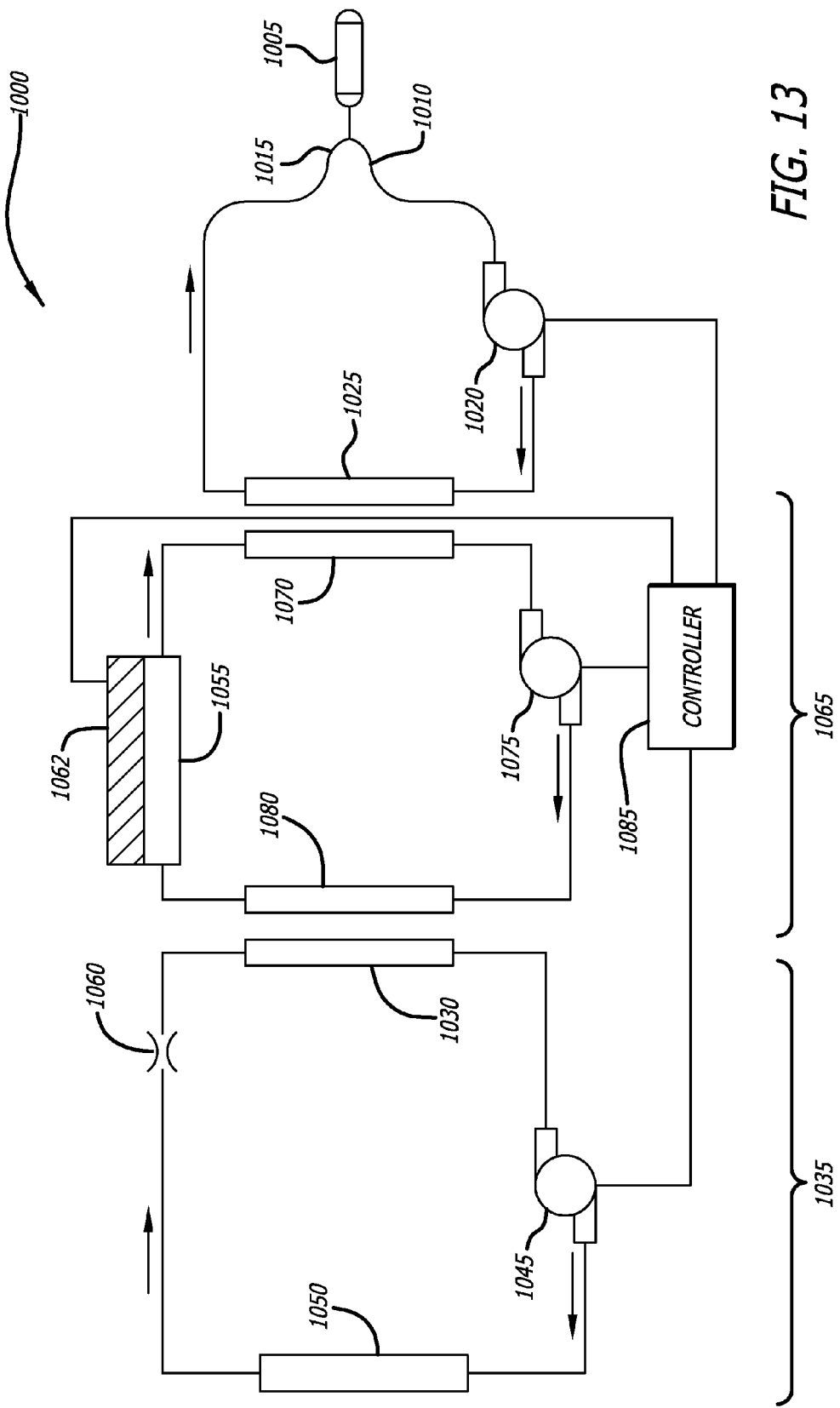
FIG. 13 is a schematic illustration of an alternative embodiment to the embodiment of FIG. 12.

FIG. 13 provides a schematic illustration of yet another embodiment of the present invention similar to that shown in FIG. 12. In this embodiment, a block 1055 is inserted into a secondary stage 1065. A thermo-electric heater/cooler 1062 is in thermal communication with block 1055. In this manner, thermo-electric heater/cooler 1062 may be used to provide additional heat removal or addition to the heat exchange fluid circulating through secondary stage 1065.

It will be also apparent from the embodiments illustrated in FIGS. 11-13 that the operation of the various pumps, compressors and thermo-electric heater/coolers may be controlled by a controller in response to signals received from temperature sensors associated with the patient, the various heat exchangers or blocks, and any operating parameters provided to the controller by the operator of the system, or which are embedded in the processor of the controller or a memory associated therewith. Various control schemes that may be used by the controller to control the operation of these embodiments have been discussed previously, and are applicable to these embodiments as well.

Description of the Pump in the Heat Exchange Fluid Circuit

As described the above, the pump that causes heat exchange fluid to flow within the fluid circuit comprising the pump, an external heat exchanger and a heat exchange catheter may take various forms. In one embodiment, the pump has a pump head 98 that is incorporated into a heat exchange cassette, as shown in FIG. 2. This pump head interacts with a pump driver mechanism 630 (FIG. 9B) when the heat exchange cassette inserted into the control unit. For example, a vane pump, gear pump or the like may be used as the pump head.

In an alternative embodiment, a peristaltic pump may be used. In this embodiment, the pump head is not incorporated into the heat exchange cassette. Instead, the rotor and motor of the peristaltic pump are mounted in the control unit console in such a fashion as to make loading tubing into the peristaltic pump mechanism relatively easy for an operator. In this embodiment, the "pump head", defined as the portion of the pump that actually drives fluid through the fluid circuit, is defined by the length of tubing that is mounted within the peristaltic pump and contacted by the roller (pump driver) of the peristaltic pump.

It should also be understood, in accordance with the present invention, that the controller processor may be configured to simultaneously respond to multiple sensors, or to activate or de-activate various components such as several heat exchangers. In this way, for example, a controller might heat blood that is subsequently circulated to the core body in response to a sensed core body temperature that is below a target temperature for the core, and simultaneously activate a second heat exchanger to cool blood that is directed to the brain region in response to a sensed brain temperature that is above a target temperature for the brain. It may be that the sensed body temperature is at the target temperature and thus the heat exchanger that is in contact with blood circulating to the body core may be turned off by the controller, while at the same time the controller continues to activate the second heat exchanger to cool blood that is directed to the brain region. Any of the many control schemes that may be anticipated by an operator and programmed into the control unit are contemplated by this invention.

A further advantage of the system of the present invention is that all of the portions of the system that are in contact with the patient are disposable, but substantial and relatively expensive portions of the system are reusable. Thus, the catheter, the flow path for sterile heat exchange fluid, the sterile heat exchange fluid itself, and the pump head are all disposable. Even if a rupture in the heat exchange balloon permits the heat exchange fluid channels and thus the pump head to come in contact with a patient's blood, no cross-contamination will occur between patients because all those elements are disposable. The pump driver, the electronic control mechanisms, the thermoelectric cooler, and the manual input unit, however, are all reusable for economy and convenience. Desirably, as illustrated, all of these re-usable components are housed within a single control unit. Likewise, the various sensors distributed around body and along the catheter may be disposable, but the controller processor to which they attach is re-usable without the need for sterilization.

It will also be appreciated by those of skill in the art that the system described herein may be employed using numerous substitutions, deletions, and alternatives without deviating from the spirit of the invention as claimed below. For example, but not by way of limitation, the serpentine pathway in the heat exchange plate may be a coil or other suitable configuration, or the sensors may sense a wide variety of body locations and other parameters may be provided to the processor, such as temperature or pressure. Further, the in-dwelling heat exchanger at the end of the catheter may be any appropriate type, such as a non-balloon heating/cooling element. An appropriate pump might be provided that is a screw pump, a gear pump, a diaphragm pump, a peristaltic roller pump, or any other suitable means for pumping the heat exchange fluid. All of these and other substitutions obvious to those of skill in the art are contemplated by this invention.

While several particular forms of the invention have been illustrated and described, it will be apparent that various modifications can be made without departing from the spirit and scope of the invention.

I claim:

1. A system for managing the temperature of a person using an intravascular heat exchanger inserted into the lumen of a body vessel of a patient, comprising:
   a refrigeration circuit comprising a compressor for pumping and compressing a first heat exchange fluid through the refrigeration circuit, a condenser, an expansion valve, and a first side of a first heat exchanger;
   a secondary fluid circuit comprising a pump for pumping a second heat exchange fluid through the secondary fluid circuit, a second side of the first heat exchanger, a first side of a second heat exchanger, and a heat exchange block;
   a reversible heater/cooler in thermal communication with the heat exchange block such that the reversible heater/cooler may modulate the temperature of the heat exchange fluid in the secondary fluid circuit by adding heat to or removing heat from the heat exchange block;
   an intravascular fluid circuit comprising an intravascular heat exchanger having a fluid input port and a fluid output port, a pump for pumping a third heat exchange fluid through the intravascular fluid circuit, and a second side of the second heat exchanger; and
   a controller having a processor configured by software commands to receive temperature indications related to the temperature of a patient from a sensor and to control operation of the heater/cooler in accordance with a target temperature.

2. The system of claim 1, wherein the fluid input and the fluid output of the intravascular heat exchanger each have releasable couplings, and wherein the second side of the second heat exchanger has an input port and an output port, the input port and output port of the second side of the second heat exchanger having releasable couplings, the releasable coupling of the input port of the second side of the second heat exchanger configured to engage the releasable coupling disposed on the fluid output of the intravascular heat exchanger and the releasable coupling of the output port of the second side of the second heat exchanger configured to engage the releasable coupling of the fluid input of the intravascular heat exchanger.

3. The system of claim 1, wherein the reversible heater/cooler is a thermoelectric element.

4. The system of claim 1, wherein the processor is further configured by software commands to control the refrigeration circuit to remove heat from the first heat exchange fluid when the difference between the sensed patient temperature and the target temperature exceeds a selected value.

5. The system of claim 1, wherein the processor is configured by software commands to control the pump of the intravascular fluid circuit when the difference between the sensed patient temperature and the target temperature exceeds a selected value.

6. The system of claim 1, wherein the processor is configured by software commands to control the heater/cooler to remove heat from the heat exchange block when the difference between the sensed patient temperature and the target temperature is less than a selected value.

7. The system of claim 1, wherein the processor is configured by software commands to control the heater/cooler to add heat to the heat exchange block when the sensed patent temperature is less than the target temperature.

8. The system of claim 4, wherein the processor is configured by software commands to control the refrigeration circuit to stop removing heat from the first heat exchange fluid and the processor is configured by software commands to control the heater/cooler to add heat to the heat exchange block when the difference between the sensed patient temperature and the target temperature is less than a selected value.

9. The system of claim 1, further comprising a communication module configured to communicate information related to the sensed temperature and the operation of the refrigeration and secondary fluid circuits to a display remote from the system.

10. The system of claim 1, further comprising a communication module configured to communicate information related to the sensed temperature and the operation of the refrigeration and secondary fluid circuits to a data management system.

11. The system of claim 10, wherein the information communicated to the data management system is associated with an electronic medical record of the patient.

12. The system of claim 1, further comprising:
   a communication module configured to communicate with a device monitoring a health parameter of the patient; and a display controlled by the processor of the controller to display information related to the operation of the refrigeration and secondary fluid circuits and information received from the monitoring device related to the monitored health parameter of the patient.

13. The system of claim 1, wherein the heater/cooler is disposed in the refrigeration circuit rather than the secondary circuit.

14. The system of claim 1, wherein the first side of the first heat exchanger is a container filed with a fourth heat exchange fluid, the container configured to receive the second side of the first heat exchanger such that the second side of the first heat exchanger is immersed in the fourth heat exchange fluid in the container.

15. The system of claim 1, wherein the first side of the second heat exchanger is a container filled with a fourth heat exchange fluid, the container configured to receive the second side of the second heat exchanger such that the second side of the second heat exchanger is immersed in the fourth heat exchange fluid in the container.

16. A system for managing the temperature of a person using an intravascular heat exchanger inserted into the lumen of a body vessel of a patient, comprising:
 a refrigeration circuit comprising a compressor for pumping and compressing a first heat exchange fluid through the refrigeration circuit, a condenser, an expansion valve, a first side of a first heat exchanger, and a heat exchange block;
 a reversible heater/cooler in thermal communication with the heat exchange block such that the reversible heater/cooler may modulate the temperature of the heat exchange fluid in the refrigeration circuit by adding heat to or removing heat from the heat exchange block;
 a secondary fluid circuit comprising a pump for pumping a second heat exchange fluid through the secondary fluid circuit, a second side of the first heat exchanger, and a first side of a second heat exchanger;
 an intravascular fluid circuit comprising an intravascular heat exchanger having a fluid input port and a fluid output port, a pump for pumping a third heat exchange fluid through the intravascular fluid circuit, and a second side of the second heat exchanger; and
 a controller having a processor configured by software commands to receive temperature indications related to the temperature of a patient from a sensor and to control operation of the heater/cooler in accordance with a target temperature.

17. The system of claim 16, wherein the first side of the first heat exchanger is a container filed with a fourth heat exchange fluid, the container configured to receive the second side of the first heat exchanger such that the second side of the first heat exchanger is immersed in the fourth heat exchange fluid in the container.

18. The system of claim 16, wherein the first side of the second heat exchanger is a container filled with a fourth heat exchange fluid, the container configured to receive the second side of the second heat exchanger such that the second side of the second heat exchanger is immersed in the fourth heat exchange fluid in the container.

* * * * *